(12) United States Patent
Rubenstein

(10) Patent No.: US 7,915,380 B2
(45) Date of Patent: Mar. 29, 2011

(54) COMPOSITIONS, SYSTEMS AND METHODS FOR THE DIAGNOSIS, PREVENTION AND TREATMENT OF DISORDERS ASSOCIATED WITH AZETIDINE-2-CARBOXYLIC ACID

(75) Inventor: Edward Rubenstein, Hillsborough, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 411 days.

(21) Appl. No.: 11/693,423

(22) Filed: Mar. 29, 2007

(65) Prior Publication Data

US 2007/0231313 A1   Oct. 4, 2007

Related U.S. Application Data

(60) Provisional application No. 60/787,267, filed on Mar. 30, 2006, provisional application No. 60/791,269, filed on Apr. 12, 2006.

(51) Int. Cl.
*C07K 7/04* (2006.01)
*A61K 38/08* (2006.01)
*C12P 21/08* (2006.01)
*C07K 16/18* (2006.01)

(52) U.S. Cl. ..... 530/328; 514/17.7; 514/17.9; 435/69.6; 530/388.1; 530/389.1; 530/389.8

(58) Field of Classification Search ................ None
See application file for complete search history.

(56) References Cited

U.S. PATENT DOCUMENTS 4,346,103 A  *  8/1982  Friedmann ............... 514/548

OTHER PUBLICATIONS

E. Rubenstein et al. Phytochem. (2009) 70, pp. 100-104.*
F.G. Mastronardi and M.A. Moscarello. J. Neurosci. Res. (2005) 80, pp. 301-308.*
J. Garriga et al. Biochem. J. (1996) 320, pp. 983-989.*
E. Rubenstein. J. Neruopathol. Exp. Neurol. (2008) 67(11), pp. 1035-1040.*
Anti-MBP Product information sheet (cat # 01417). Stemcell Technology, Inc. 1 page. Revised Jan. 2003.*
C.C. Bernard, et a. Clin. Exp. Immunol. (1983) 52, pp. 98-106.*

* cited by examiner

*Primary Examiner* — Andrew D Kosar
(74) *Attorney, Agent, or Firm* — Thomas, Kayden, Horstemeyer & Risley, LLP

(57) ABSTRACT

Methods and systems for detecting azetidine-2-carboxylic acid (Aze) in food consumable by humans and animals are provided. Also provided are methods and systems for inactivating Aze in food and byproducts, as well as other methods for the diagnosis, prevention, and treatment of disorders associated with Aze.

1 Claim, 6 Drawing Sheets proline    azetidine-2-carboxylic acid

COMPOSITIONS, SYSTEMS AND METHODS FOR THE DIAGNOSIS, PREVENTION AND TREATMENT OF DISORDERS ASSOCIATED WITH AZETIDINE-2-CARBOXYLIC ACID

CROSS-REFERENCE TO RELATED APPLICATION

This application claims priority to and the benefit of copending U.S. provisional patent application entitled "Methods for the Diagnosis, Prevention and Treatment of Disorders Associated with Azetidine-2-Carboxylic Acid", Ser. No. 60/787,267, filed Mar. 30, 2006 and U.S. provisional patent application of the same title having Ser. No. 60/791,269, filed Apr. 12, 2006, both of which are incorporated herein by reference in their entirety.

FIELD OF THE INVENTION(S)

The present disclosure relates to the diagnosis, prevention, and treatment of diseases associated with and/or caused by exposure to or ingestion of the nonprotein amino acid azetidine-2-carboxylic acid.

BACKGROUND

Although bacteria, plants and animals construct their proteins from the same set of 20 amino acids (22, including selenocysteine and pyrolysine), there are in nature a large number of other amino acids that are not incorporated into peptides or proteins. Such compounds, for which there are no codons, are referred to as nonprotein amino acids.

Many of these compounds serve as sentries that protect vital plant structures by poisoning predators. Plants that tend to harbor nonprotein amino acids include the Fabaceae (e.g., legumes, beans, peas, peanuts, soy, clover, some trees), the Curcurbitaceae (e.g., gourds, pumpkins, cucumbers), as well as fruits (e.g., apple, banana, cherry, cranberry, date, pear) and nuts (e.g., almond, pine nut, walnut), and Chenopodiaceae (e.g., beets). The consumption of most of these foods/plants in usual amounts causes no apparent harm to humans; however, the ingestion of some nonprotein amino acids leads to a variety of disease states, some of which can be lethal.

Azetidine-2-carboxylic acid (Aze) is a plant nonprotein amino acid identical to proline except that the ring of Aze has four members and the ring of proline has five, as illustrated in FIG. 1, proline (left) and Aze (right). The tRNAs of numerous species do not discriminate between Aze and proline, and therefore Aze is misincorporated in place of proline into proteins, including those of humans. Such misassembly can result in disorders owing to protein malformation, dysfunction, and immunogenicity. In addition, in various studies Aze administration has resulted in a wide range of teratogenic effects in chicks, ducks, hamsters, mice, and rabbits.

Since Aze was not believed to be a constituent of the human diet, its role in the pathogenesis of disease in humans has remained unexplored. However, Aze has shown to be present in sugar beets and in table beets (*Beta vulgaris*). Sugar beet agriculture, especially in the Northern Hemisphere, has become widespread during the past 150 years, and now accounts for nearly 30 percent of the world's supply of sucrose. Sugar beet byproducts are used as a dietary supplement for some livestock, therefore opening a channel for the possible entry of Aze into the human food chain.

The intrusion of Aze into the food chain would have significant implications regarding disease in humans. The misincorporation of Aze in place of proline may be especially pathogenetic when the malformed protein is involved in critical functions such as DNA repair or embryogenesis. Proteins in which there are silent genetic mutations may become disease-producing should acquired misassembly owing to Aze substitution for proline also occur. Furthermore, long-lived proteins, such as collagen and myelin basic protein, may become sinks into which endogenously re-circulating Aze, as well as exogenous dietary Aze, eventually accumulate.

Therefore, if Aze is, in fact, entering the human food chain, there is a critical need for methods and systems for detecting Aze in both human and animal foodstuffs as well as methods and systems for treating food consumable by humans and animals to remove or otherwise inactivate Aze. What is further needed are methods and systems for detecting Aze in human proteins, diagnosing disorders associated with Aze, and treating disorders associated with Aze.

SUMMARY

Briefly described, the present disclosure provides methods and systems for preventing, detecting, diagnosing, and treating conditions associated with misincorporation of Aze into host proteins. First, in order to help prevent such conditions by preventing or reducing the possibility of such misincorporation by reducing host exposure to Aze, methods for detecting Aze in food consumable by humans or animals are provided. For instance, methods of detecting Aze in garden and sugar beets, animal feed, and animal products produced from animals fed materials containing Aze are provided.

Other embodiments of the present disclosure provide methods for inactivating Aze in food consumable by humans or animals (e.g., beets or beet byproducts). One embodiment includes heating the food containing Aze or an ingredient of food containing Aze to a temperature of about 100 degrees C. to 200 degrees C., where the heat is effective to rupture the ring-structure of Aze. Another embodiment of inactivating Aze in food includes contacting the food with an effective amount of Aze acetyltransferase, where the Aze acetyltransferase inactivates Aze by acetylation.

One embodiment of a method of reducing the harmful effects of Aze consumption in a host includes administering to a host who has recently consumed material containing Aze a therapeutically effective amount of a composition including proline, where the proline is effective to reduce the amount of Aze incorporated into host (or fetal) proteins such as, but not limited to, myelin basic protein, collagen, hypoxia-inducible factor, profilins, ion channel proteins, vesicular glutamate transporters, and hemoglobins.

In other embodiments of the present disclosure, methods of treating a disorder associated with Aze are provided. Exemplary embodiments include administering to a host in need of treatment for a disorder associated with Aze a therapeutically effective amount of a composition including proline, where the proline is effective to reduce the amount of Aze incorporated into host proteins or to prevent additional incorporation of Aze into host proteins. Disorders treatable by such methods may include, but are not limited to: multiple sclerosis, rheumatoid arthritis, systemic lupus erythematosus, systemic scleroses, mixed connective tissue disorders, and inflammatory myopathies and vasculitides. In particular, exemplary disorders treatable by such methods include auto-immune disorders.

Methods of the present disclosure also include methods of detecting Aze in host polypeptides. Exemplary methods of detecting Aze in host polypeptides include obtaining a sample from a host, where the sample includes host polypeptides, and contacting the host sample with a composition including at least one anti-Aze antibody, where the at least one anti-Aze antibody recognizes at least one host polypeptide having Aze in place of proline in the polypeptide sequence. Also provided are methods of detecting antibodies to Aze in a host including the following steps: providing at least one peptide comprising Aze, where the peptide is a derivative of a wild-type peptide having at least one proline residue replaced by Aze; providing a sample from a host, where the sample includes host antibodies; contacting the host sample with the at least one peptide; and detecting binding between the peptide and an antibody from the host sample, where binding indicates the presence of an antibody to the Aze-containing peptide.

Additional embodiments of methods of detecting antibodies to Aze include: providing a library of peptides having Aze in place of at least one proline residue; contacting the library of peptides with a composition including antibodies; and detecting binding between the peptides and an antibody from the antibody composition, where binding indicates the presence of an antibody to the Aze-containing peptide. In an exemplary embodiment the library of peptides includes at least one of the peptides of SEQ. ID. NOS. 2-8. In embodiments, the library of peptides includes portions of one or more of the following human proteins: myelin basic protein, collagen, hypoxia-inducible factor, profilins, ion channel proteins, vesicular glutamate transporters, and hemoglobins, where the wild-type sequence of each protein portion has at least one proline residue, and where at least one such proline of each peptide in the library has been replaced by Aze.

Embodiments of the present disclosure further include polypeptides including a sequence selected from SEQ. ID. NOS. 2-8 as well as antibodies capable of binding a polypeptide having a sequence selected from: SEQ. ID. NOS. 2-8.

The details of some exemplary embodiments of the methods, compositions, features, and systems of the present disclosure are set forth in the description below. Other features, objects, and advantages of the disclosure will be apparent to one of skill in the art upon examination of the following description, drawings, examples and claims. It is intended that all such additional systems, methods, compositions, features, and advantages be included within this description, be within the scope of the present disclosure, and be protected by the accompanying claims.

BRIEF DESCRIPTION OF THE DRAWINGS

The disclosure can be better understood with reference to the following drawings. The components in the drawings are not necessarily to scale, emphasis instead being placed upon clearly illustrating the principles of the present disclosure. The drawings are described in greater detail in the description and examples below.

DETAILED DESCRIPTION

Figure 1:
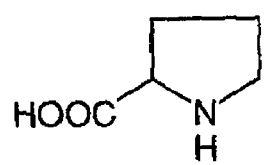
FIG. 1 illustrates the chemical structure of proline (left) and azetidine-2-carboxylic acid (Aze) (right).
Figure 1:
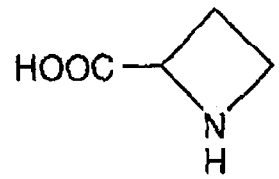

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Embodiments of the present disclosure will employ, unless otherwise indicated, techniques of medicine, pharmacology, biochemistry, molecular biology, genetics, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

DEFINITIONS

The terms "native," "wild type", or "unmodified" polypeptide, protein or enzyme, are used herein to provide a reference point for the polypeptide, protein, or enzyme prior to any modification, mutation, and the like, as described herein. Typically, the unmodified, native, or wild type polypeptide, protein, or enzyme has an amino acid sequence that corresponds substantially to the amino acid sequence of the polypeptide, protein, or enzyme as it generally occurs in nature and/or in vivo.

The term "residue" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

As used herein, "polynucleotides" include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 100 nucleotides in length, while a "polynucleotide" includes a nucleotide multimer having any number of nucleotides greater than 1, although they are often used interchangeably.

It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., diaminopurine and its derivatives, inosine and its derivatives, alkylated purines or pyrimidines, acylated purines or pyrimidines, thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N-6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in the present disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in the following references: Computational Molecular Biology, Lesk, A. M., Ed., Oxford University Press, New York, 1988; Biocomputing: Informatics and Genome Projects, Smith, D. W, Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the *Needelman and Wunsch*, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

An "enzyme," as used herein, is a polypeptide that acts as a catalyst, which facilitates and generally speeds the rate at which chemical reactions proceed but does not alter the direction or nature of the reaction.

As used herein, the term "promoter" includes all sequences capable of driving transcription of a coding sequence. In particular, the term "promoter" as used herein refers to a DNA sequence generally described as the 5' region of a gene, located proximal to the start codon. The transcription of an adjacent gene(s) is initiated at the promoter region. The term "promoter" also includes fragments of a promoter that are functional in initiating transcription of the gene.

A "primer" as used herein generally refers to a nucleic acid strand, or a related molecule, that serves as a starting point for replication, and is used in amplification techniques, such as the polymerase chain reaction (PCR). Primers used in such techniques are usually relatively short (generally about 20-50 base pairs), artificially synthesized polynucleotide strands. In PCR, primers are used to select the polynucleotide sequence to be amplified by the PCR process.

The term "expression" as used herein describes the process undergone by a structural gene to produce a polypeptide. It is a combination of transcription and translation.

The term "plasmid" as used herein refers to a non-chromosomal double-stranded DNA sequence including an intact "replicon" such that the plasmid is replicated in a host cell.

As used herein, the term "vector" or "expression vector" is used in reference to a vehicle used to introduce a nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

The term "transformation" refers to the introduction of DNA or RNA into cells in such a way as to allow gene expression.

The term "coupled" as used herein refers to the binding, bonding, or other forms of association of a protein, specifically the association of a protein having an active site and a substrate or ligand.

As used herein, the term "host" or "organism" includes both humans, mammals (e.g., cats, dogs, horses, etc.), and other living species that are in need of treatment for conditions/diseases. A living organism can be as simple as, for example, a single eukaryotic cell or as complex as a mammal.

The term "composition" can include one or more chemical compounds.

The term "derivative" refers to a modification to the disclosed compounds including, but not limited to, hydrolysis, reduction, or oxidation products, of the disclosed compounds, as well as mutations to the disclosed polypeptides. Hydrolysis, reduction, and oxidation reactions are known in the art.

The term "functional derivative" refers to a derivative of the disclosed compounds that retains the function of the disclosed compound, although not necessarily at the same level of functionality (e.g., the variant may have enhanced, reduced or changed functionality, so long as it retains the basic function).

The term "therapeutically effective amount" as used herein refers to that amount of the compound being administered which will relieve or prevent to some extent one or more of the symptoms to be treated. In reference to conditions/diseases caused directly or indirectly by exposure to Aze, a therapeutically effective amount refers to that amount which has the effect of preventing the condition/disease from occurring in an animal that may be predisposed to the disease but does not yet experience or exhibit symptoms of the condition/disease (prophylactic treatment), alleviation of symptoms of the condition/disease, diminishment of extent of the condition/disease, stabilization (e.g., not worsening) of the condition/disease, preventing the spread of condition/disease, delaying or slowing of the condition/disease progression, amelioration or palliation of the condition/disease state, and combinations thereof.

"Pharmaceutically acceptable salt" refers to those salts that retain the biological effectiveness and properties of the free bases and which are obtained by reaction with inorganic or organic acids such as, but not limited to, hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples of excipients include, but are not limited to, calcium carbonate, calcium phosphate, various sugars and types of starch, cellulose derivatives, gelatin, vegetable oils, and polyethylene glycols.

As used herein, "treat", "treating", and "treatment" are an approach for obtaining beneficial or desired clinical results. For purposes of embodiments of this disclosure, beneficial or desired clinical results include, but are not limited to, preventing the condition/disease from occurring in an animal that may be predisposed to the condition/disease but does not yet experience or exhibit symptoms of the disease (prophylactic treatment), alleviation of symptoms of the condition/disease, diminishment of extent of the condition/disease, stabilization (e.g., not worsening) of the condition/disease, preventing spread of the condition/disease, delaying or slowing of the condition/disease progression, amelioration or palliation of the condition/disease state, and combinations thereof. In addition, "treat", "treating", and "treatment" can also mean prolonging survival as compared to expected survival if not receiving treatment.

As used herein, the term "topically active agents" refers to compositions of the present disclosure that elicit pharmacological responses at the site of application (contact) to a host.

As used herein, the term "topically" refers to application of the compositions of the present disclosure to the surface of the skin and mucosal cells and tissues.

As used herein, the term "inhibit" and/or "reduce" generally refers to the act of reducing, either directly or indirectly, a function, activity, or behavior relative to the natural, expected, or average or relative to current conditions. For instance, something that inhibits or reduces incorporation of Aze into a host protein might interfere with, stop, or slow such incorporation. For instance, if a certain action or composition is said to reduce incorporation of Aze into a host protein, this may indicate reducing such incorporation below what would be expected if the action had not been taken or the composition had not been administered.

As used herein, the term "modulate," "modify," and/or "modulator" generally refers to the act of directly or indirectly promoting/activating or interfering with/inhibiting a specific function or behavior. In some instances a modulator may increase and/or decrease a certain activity or function relative to its natural state or relative to the average level of activity that would generally be expected or relative to a current level of activity.

As used herein, the term "disorder" includes both conditions and diseases of a host (e.g., a human or other mammal). Additionally, a disorder "associated with Aze" or "mediated by Aze" indicates that the disorder is somehow linked with the misincorporation of Aze into host proteins. The misincorporation of Aze into the host proteins may not directly cause the disease or condition, but it may trigger, enhance, or otherwise influence the state, progression, or incidence of the disease or condition. As used herein "misincorporation" of Aze into a host protein refers to the replacement of a proline residue by Aze in a host protein.

As used herein "auto-immune disorder" refers to certain diseases and/or conditions in which a host's immune system attacks the host's own cells and/or tissues. Exemplary auto-immune disorders include multiple sclerosis, lupus, rheumatoid arthritis, and the like.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins or the nucleic acid may be incorporated into a vector or a chromosome. A "transformed" cell is thus a cell transfected with a nucleic acid sequence.

The term "recombinant" generally refers to a non-naturally occurring nucleic acid, nucleic acid construct, or polypeptide. Such non-naturally occurring nucleic acids include combinations of DNA molecules of different origin that are joined using molecular biology technologies, or natural nucleic acids that have been modified, for example that have deletions, substitutions, inversions, insertions, etc. Recombinant also refers to the polypeptide encoded by the recombinant nucleic acid. Non-naturally occurring nucleic acids or polypeptides include nucleic acids and polypeptides modified by man.

As used herein, the term "selectable marker" refers to a gene product that confers a selectable phenotype, such as antibiotic resistance, on a transformed cell or organism (e.g., a plant). Selectable markers are encoded by expressible DNA sequences, which are sometimes referred to herein as "selectable marker genes."

As used herein, the term "promoter" or "promoter region" refers to the 5' regulatory regions of a gene, including promoters per se, as well as other transcriptional and translational regulatory sequences.

The term "operably linked" indicates that the regulatory sequences necessary for expression of the coding sequences are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "transgene" refers to an artificial gene which is used to transform a cell of an organism, such as a bacterium or a plant.

Having defined some of the terms herein, the various embodiments of the disclosure will be described.
General Discussion:

The ingestion of or exposure to azetidine-2-carboxylic acid (Aze) may result in various conditions and/or diseases in forms, such as, but not limited to: congenital malformations; autoimmune disorders, especially those involving long-lasting structural proteins such as collagen and myelin basic protein; disorders of ion channels; disorders of other molecules in which proline plays a critical structural or functional role, such as hypoxia-inducible factor, profiling, and the hinge region of immunoglobulins; and degenerative diseases, again especially those related to defective mechanical properties of collagen and related molecules in bones, joints, tendons, and supportive structures.

Thus, the present disclosure is directed to compositions and methods for treating or preventing conditions associated with exposure to Aze, whether by elimination or reduction of Aze in the environment, testing for the presence of Aze in foodstuff and other materials, amelioration of the effects of Aze, methods to determine susceptibility to Aze related disorders, and/or tools for studying the relation of Aze to various diseases and conditions.

Aspects, compositions, methods, features, and advantages of the present disclosure will be or become apparent to one with skill in the art upon examination of the following drawings and detailed description. It is intended that all such compositions, methods, features, and advantages be included within this description, be within the scope of the present disclosure.

Azetidine-2-Carboxylic Acid (Aze)

Fowden demonstrated that azetidine-2-carboxylic acid can be incorporated into proteins in place of proline. (Fowden L., Richmond M. H. [1963] Biochem. Biophys. Acta 71:450-61, which is hereby incorporated by reference herein). In principle, azetidine-2-carboxylic acid can replace proline in any protein, altering its structure, including its folding, or altering its function or creating new epitopes. Thus, the misincorportation of azetidine-2-carboxylic acid results in disease states owing to malformation of, dysfunction of, and expression of novel epitopes on peptides or proteins. Such events occurring during embryogenesis lead to various disorders including congenital malformations. Misincorporation is the result of the inability of some prolyl-tRNA synthetases to discriminate between proline and azetidine-2-carboxylic acid.

Azetidine-2-Carboxylic Acid in Food

Azetidine-2-carboxylic acid was first isolated from Liliaceae by Fowden in 1956, who later confirmed that azetidine-2-carboxylic acid was present in sugar beets. Sugar beets are processed for their high concentration of sucrose, and their by products are used as feed for livestock and other animals. Fodder beets are fed to livestock. The identification of azetidine-2-carboxylic acid as a substantial constituent of the amino acids in garden beets was made by E. Rubenstein, H. Zhou, K. M. Krasinska, A. Chien, and C. H. Becker, (as disclosed in "Azetidine-2-carboxylic acid in garden beets (*Beta vulgaris*)" Phytochemistry, March 2006, which is hereby incorporated by reference).

Garden beets are a popular table food, and are eaten in many regions of the world. The widespread consumption of garden beets elevates them to the status of a staple in a number of heavily populated regions. As already mentioned, sugar beets are not only used for the production of sucrose and certain forms of molasses, but also are an important component of the diet of dairy and meat-producing livestock, including cattle, sheep, and pigs. Thus, to the extent that azetidine-2-carboxylic acid finds its way from beets into the feed of such animals, their milk, their milk products, and their meat serve as secondary sources of azetidine-2-carboxylic acid in the food consumed by humans and other animals. However, to date no studies have investigated the presence of Aze in any such food products. The presence of Aze in milk and baker's yeast is demonstrated in Example 1, below. This shows that Aze is indeed present in the human food chain, which raises critical health concerns and demonstrates a need for food testing systems and procedures for testing food for Aze levels.

Some Teratogenic and Toxic Effects of Azetidine-2-Carboxylic Acid

In laboratory experiments, azetidine-2-carboxylic acid has been shown to interfere with a number of biological processes; however, the pathogenetic role of azetidine-2-carboxylic acid has not been recognized in human or veterinary medicine.

The introduction of azetidine-2-carboxylic acid into a protein in place of proline causes conformational changes. For instance, altered bond angles and have been shown to change the tertiary structure of a collagen strand. Such effects have been identified in various tissues. Exposure to the compound in mice has caused the failure to form normal basal lamina of mammary epithelial cells, suppressing the activity of calcium-binding proteins needed for cell spreading. In the same animal model, the proline analogue disrupts collagen secretion and results in dysgenesis of the embryonal otic elements.

Azetidine-2-carboxylic acid has been responsible for arrested lung growth and impaired secretion of surfactant in embryonic rats and mice. Similarly, hepatic collagen synthesis has been inhibited in murine schistosomiasis. The hair of mice fed azetidine-2-carboxylic acid exhibits abnormal physical properties resulting from alterations of the helical structure of keratin.

Numerous studies have been conducted on skin. Abnormal biochemical, mechanoelastic, and structural changes have been observed in murine dermal collagen I. In human skin, impaired fibroblast growth has been noted, and procollagen has been found in non-triple-helical conformations. In pigs, the nonprotein amino acid has been associated with delayed wound healing. Abnormal development of murine dental structures includes failure of ligamentous growth, abnormalities of fibroblasts and osteoblasts, and delayed morphogenesis.

Azetidine-2-carboxylic acid has replaced proline in human and in rabbit hemoglobin. The nonprotein amino acid has substituted for proline in synthetic peptides such as oxytocin and vasopressin. Abnormal somite mesenchyme differentiation, defective chondrogenesis, impaired bud development, and absent vertebra in chick embryos, along with abnormal development of the avian neural crest leading to failure of osteogenesis of the mandibular process, have implications about the deleterious effects of the compound on early neural differentiation and growth. Abnormal uropygial development in duck embryos has also been observed. Other anatomic abnormalities induced by the nonprotein amino acid in chicks include interference with thyroid histogenesis and failure of differentiation of the testis. Tendon abnormalities such as absence of normal triple helix formation of collagen and increased collagen glycosylation have also been observed in chicks. Azetidine-2-carboxylic acid fed to pregnant mice predisposes to cleft palate. Exposure during pregnancy in hamsters has been reported to result in fetal weight abnormalities, tissue hemorrhages, cleft palate, retarded ossifications, and shortened bones.

Administration of the nonprotein amino acid has induced the formation of novel proteins including heat shock proteins in human and avian tissues. Azetidine-2-carboxylic acid causes misfolding of proteins. The compound has been found to induce the expression of heat shock factor-regulated genes in yeast.

Thus, ingestion of, or other exposure to, azetidine-2-carboxylic acid by humans and other animals can result in abnormal embryogenesis, congenital anomalies, and structural and functional changes in peptides, proteins, cells, tissues, and organs. This raises the need for diagnostic tests and methods for detecting Aze present in host proteins, as well as methods and compositions for reducing the incorporation of ingested Aze into host proteins.

Role of Proline in Proteins and Implications for Disease Pathogenesis

Proline is unlike any of the other 22 protein amino acids in that its amino group is covalently locked within a five-member ring, as shown in FIG. 1. Such bonding constrains the torsion angles of the peptide union between the nitrogen group of a proline and the carboxyl group of the adjacent amino acid. Therefore such bonds impart a rigid flexure at that point in a string of amino acids. In the peptide union between other amino acids, the nitrogen atom of the amino group of one and the hydrogen atom of the carboxyl group of the other occupy opposite positions (trans) in the plane of the peptide bond. Because of the unique electron environment of proline's nitrogen, there is a strong tendency for the hydrogen and oxygen atoms to be on the same side of the plane (cis), a configuration that causes significant changes in bond angles, altering regional conformation. The process of cis-trans isomerization converts minor changes in the electronic milieu into major mechanical events, transduced by proline. Another exceptional property of proline is that its nitrogen is bonded to only one hydrogen atom, and therefore proline cannot function as a hydrogen bond donor, and can serve only as a hydrogen bond acceptor.

These properties account for the special role of proline in molecular structure and function, features that resulted in the evolutionary selection of proline, among hundreds of other naturally occurring amino acids, as one of the set of protein amino acids, distinguished by the existence of a DNA codon that directs their incorporation into proteins.

Because of the bond angle flexures, a proline residue often changes the direction of a chain and results in a turn. Some proline-rich sequences create a characteristic extended helix, which is the configuration a strand in collagen. On the other hand, the intrusion of a proline disrupts the basic architecture of alpha helices or beta sheets. Prolines can serve as the initial amino acid of alpha helices and at the edges of beta sheets.

Due to proline's powerful effects on protein architecture, as described above, the displacement of a proline by a molecular analogue, such as Aze, may result in untoward effects on the conformation, charge distribution and function of a protein. The adverse phenotypic effects of replacing proline with another amino acid are a likely explanation for the fact that such substitution is probably the least frequent type of hereditary point mutation. A compilation of such mutations indicates the replacement of proline by another amino acid accounts for only 224 of a total of 12,648 changed residues in mutation sites.

Transient exposure to Aze, leading to misincorporation into proteins that are turned over rapidly, may not have severe ramifications, unless the molecule is engaged in critical activities such as those involved in embryogenesis and DNA repair. Misincorporation into proteins with long lifetimes can have critical consequences. The degradation of short-lived molecules leads to the endogenous release of the foreign molecules, their recirculation, and successive rounds of misincorporation. Catabolic states are likely to result in increased internal release. This cycle pauses when the nonprotein amino acids become engaged in the synthesis of protein with a long lifetime, where they lurk in residence and are poised to do their damage. Thus, long-lived proteins become a sink into which the foreign molecules accumulate. The gradual accretion of a nonprotein amino acid is likely to have its deleterious effects on durable proteins, typified by collagen and myelin basic protein, molecules that are laid down to a considerable extent during morphogenesis, childhood and adolescence, a time span of apparent health, during which silent events may predestine future disease.

Consumed at critical times during early pregnancy, azetidine-2-carboxylic acid increases the risk of a variety of congenital abnormalities. A small stream of the nonprotein amino acid entering human protein synthesis can result in the gradual accumulation of abnormally formed, dysfunctional, and immunogenic molecules. The consequences can be especially severe in the case of proteins with a long half-life, such as collagen.

Thus, the clinical expression of disease, including autoimmune disorders such as multiple sclerosis, may not be apparent until years or even decades after the ingestion begins. In the case of an autoimmune disorder, after a critical epitopic exposure threshold is reached, the disease phase begins and may simmer or exacerbate periodically thereafter indefinitely. The continued ingestion of small quantities of the pathogenetic agents may result in lifelong illness. (Rubenstein, E. [2000] Medicine, 79:80-89).

Misincorporation can also occur in immuno-proteins and in the soluble and cellular mediators of the immune system. Multiple sclerosis serves as an exemplar of a disorder that can arise as a result of misincorporation of a nonprotein amino acid, such as azetidine-2-carboxylic acid. The disease is a relapsing or chronically recurring demyelinating disorder of the central nervous system. There is strong evidence that both genetic and environmental factors participate in its pathogenesis. (Lindsay and Wolinsky, Demyelinating Diseases, in Scientific American Medicine, Dale and Federman; eds, WebMD Inc., New York, 2003, 11:IX:1-12. Rosati G. [2001] Neurol. Sci. 22:117-139). Therefore, this demonstrates a critical need for methods and systems for determining the role of Aze in human disease, as well as methods and systems for diagnosing and treating such diseases. In particular, there is a need for methods and systems for determining the effect of Aze misincorporation into a host's proteins and polypeptides, and for treating related disorders. The importance of proline in several proteins, and some implications related to its replacement by Aze, are described below.

Possible Effects of Misincorporation of Aze for Proline in Exemplary Proteins

Laboratory data have established the pathogenic potential of Aze displacement of proline in some proteins where proline plays a significant role. A few examples, chosen to illustrate the diverse manifestations of this disease mechanism, include studies involving ion channels, collagen, hemoglobin, and hypoxia-inducible factor.

a. Ion Channels:

In neurotransmitter gated ion channels of the Cys-loop receptor superfamily, a proline residue in the apex of the loop between two transmembrane helices links receptor binding to the gating of the channel through a cis-trans isomerization. Thus, this proline serves as swivel point that exerts a nozzle-like action on the opening and closing of the channel pore.

Substituting Aze for proline in this position has been shown to impair channel function. (Lummis et al., Cis-trans isomerization at a proline opens the pore of a neuro-transmitter-gated ion channel. Nature, 2005, 438: 248-52). Fluctuating blood levels of Aze, arising from exogenous intake or endogenous release, may play a role in precipitating sporadic episodes of intermittent disorders that may be caused by dysfunction of ion channels, such as epilepsy, myopathies, migraine, and arrhythmias.

b. Collagens:

The collagens are long, thin molecules comprised of three helical chains which wrap around each other in a braided fashion. They are the most abundant protein of mammals, and may account for as much as 30% of the proteins in a human body. There are distinctive types of collagen in various tissues, such as bone, cartilage, skin, blood vessels, and the viscera. Proline constitutes about 15 percent of the amino acid residues. The prolyls become hydroxylated at the C-4 position in nascent collagen strands in a reaction catalyzed by prolyl hydroxylase. Steric repulsion between the bulky rings of proline and hydroxyproline, which are on the outside of the molecule, stabilizes the triple helix structure. There are no hydrogen bonds within a strand, but the strands are hydrogen bonded to each other.

Because of the abundance of prolyls in collagen and their critical role in its conformation, collagen molecules are highly vulnerable to the effects of the misincorporation of Aze. This is especially true during the time span of embryonic biosynthesis and growth into adulthood. Numerous studies have demonstrated that Aze exposure causes severe impairment of collagen formation in chicks, mice, pigs, and humans. (Rubenstein, Biologic effects and clinical disorders caused by nonprotein amino acids. Medicine, 2000, 79:80-89). Just as many proline residues in newly synthesized collagen become hydroxylated to form hydroxyproline, Aze hydroxylation has been identified in epi-hydroxymugineic acid, suggesting that such hydroxylation of Aze may occur within misassembled collagen as well. (von Wirén et al., Hydroxylated phytosiderophore species possess an enhanced chelatestability and affinity for iron (III), Plant Physiol., 2000 124:1149-57). Due to the widespread use of collagen in the body and the abundance of proline in collagen, misincorporation of Aze into collagen could lead to a wide variety of disorders.

c. Hemoglobins:

Aze has been shown to be misincorporated into human hemoglobin in place of proline. (Rubenstein, 2000). There are at least ten well-defined hemoglobinopathies associated with proline mutations. (OMIM, Number 63903, Johns Hopkins University, Baltimore, Md., Jun. 20, 2006). Some have deleterious effects on gas exchange, and some of these hemoglobins are unstable and associated with severe hemolytic disease. In addition, the misincorporation of Aze in place of proline in other hemoglobinopathies may contribute to clinical exacerbations. The factors that trigger such events are often difficult to identify.

d. Hypoxia Inducible Transcription Factors

Many of the sub-molecular details of an oxygen-sensing and hypoxia-correcting complex cellular mechanism in organisms ranging from nematodes to man have recently been elucidated. Prolyl residues play a critical role in the regulation of the HIF mechanism. (Schofield and Ratcliffe, Oxygen sensing by HIF hydroxylases. Nat. Rev. Mol. Cell. Biol. 2004, 5: 343-54).

An entire repertoire of interacting molecules is involved in the tightly coordinated activities of the HIF mechanism. These can be assigned to three general functions: hypoxia sensing, upregulation of hypoxia-correcting DNA coding sequences, and the prompt proteolytic destruction of the key components of the system after local hypoxia has been ameliorated.

HIF is a heterodimer comprised of two basic subunits, each a helix-loop-helix protein, referred to as HIFα and HIFβ. The dimer binds to DNA protein coding regions and upregulates the transcription of 40 or more proteins that correct the effects of local hypoxia. These products subserve three categories of response: increased production of vascular endothelial growth factor, increased production of erythropoietin, and increased production of the cascade of enzymes involved in glycolysis. HIFα exists in three forms. HIF 1α and HIF 2α are closely related and are rapidly induced by hypoxia; HIF 3α displays structural differences and its regulation is unclear. HIFβ is a constitutively produced nuclear transcription protein.

HIF 1α and HIF 2α contain two independently functioning oxygen-dependent degradation domains as well as two transactivation regions. HIF 1α subunits are highly inducible by hypoxia. Both HIF 1α and HIF 2α are proteolyzed within two separate oxygen-dependent degradation domains, sequences located in the central region of the molecule. HIF 1α and HIF 1β also encompass two transactivation regions, whose function and inactivation are incompletely understood. HIF 1α appears to be inactivated by an independent mechanism that excludes it from the nucleus in the presence of oxygen. HIFα subunits contain sequences that respond to hypoxia, to cobaltous ions, and to iron chelators. Each of the three HIFα regions that respond to hypoxia do so as a result of oxygen-dependent enzymatic hydroxylation of specific proline residues.

Three 2-oxoglutarate-dependent oxygenases with the capacity to catalyze HIF-prolyl hydroxylation have been identified. They have an absolute requirement for molecular oxygen as a co-substrate and therefore provide a direct link between oxygen availability and the regulation of HIF. The prolyl 4-hydroxylases regulate the HIFs by hydroxylating a Leu-Xaa-Xaa-Leu-Ala-Pro motif (SEQ. ID. NO. 9). Substitution of the proline by azetidine-2-carboxylic acid or by 3,4 dehydroproline, but not any other residue, leads to a high rate of uncoupled 2-oxoglutarate decarboxylation with no hydroxylation.

Hydroxylation of prolyl residues regulates interactions with the von Hippel-Lindau suppressor (pVHL), the component of the ubiquitin-ligase complex that designates HIFα subunits for proteasomal destruction. Hydroxylation increases the affinity of HIFα peptides for the pVHL-elongin B-elongin C (VBC) complex by a thousand-fold. The critical difference between the hydroxylated and non-hydroxylated residues is the formation of two hydrogen bonds between the alcohol of the hydroxylated prolines and two residues of pVHL. Under hypoxic conditions, prolyl hydroxylation is suppressed, and therefore the HIFα subunit escapes pVHL-mediated destruction and promptly accumulates to high levels.

Genetic abnormalities of the von Hippel-Lindau tumor suppressor-elongin proteins have been associated with benign and malignant neoplasms including renal cell carcinoma, pheochromocytoma, pancreatic tumors, and retinal, cerebellar, and spinal hemangioblastomas. (OMIM Number 193300, Johns Hopkins University, Baltimore, Md., Sep. 26, 2006). Thus, misincorporation of Aze into HIF proteins can interfere with the hydroxylation, and therefore the activity of HIF, including its interactions with other critical proteins, such as pVHL, which may lead to various disorders.

e. Profilins

Profilins regulate the assembly of actin and thus participate in cell motility and help determine cell shape. One type of profilin is found in brain cells. Profilins modulate the equilibrium between G-actin monomers and F-actin polymers. Their function depends upon an interaction with specific polyproline helices containing a motif with five or more consecutive prolyl residues. (Holt and Koffer, Cell motility: proline-rich proteins promote protrusions. Trends Cell Biol., 2001, 11:38-46). Profilins play a central role in chemotactic responses, cell division, embryogenesis, and neuronal differentiation. Therefore, misincorporation of Aze into profilins could have dramatic effects on the structure and function of these proteins resulting in a host of possible disorders.

f. Vesicular Glutamate Transporters

Another class of proline-rich proteins are the vesicular glutamate transporters. These are involved in the regulation of the amount of glutamate in a synapse. Glutamate is the main excitatory neurotransmitter in the central nervous system (CNS); glutamate transporters are required in the CNS to modulate its functioning. Since glutamate does not diffuse across the blood brain barrier, an active transporter is required. The transporters interact with proteins (endophilins) in excitatory vesicle formation. Therefore, misincorporation of Aze in place of one or more proline residues in a vesicular glutamate transporter protein could negatively affect the transporter's ability to transport glutamate across the blood brain barrier and thereby result in various disorders of the central nervous system due to a reduction in the available amount of glutamate.

g. Myelin Basic Protein

As will be discussed in greater detail below, abnormalities of myelin basic protein, a principal protein of myelin sheaths that insulate axons in the central nervous system, may underlie multiple sclerosis. (see, for instance: Boggs J M, Myelin basic protein: a multifunctional protein. Cell Mol. Life Sci., 2006, 63:1945-61; Musse et al., Diminution of membrane-bound myelin basic protein in multiple sclerosis exposes an immunodominant eptiope, Proc. Natl. Acad. Sci., USA, 2006, 103: 4422-7; and Ridsdale et al., Three-dimensional structure of myelin basic protein. II. Molecular modeling and considerations of predicted structures in multiple sclerosis. J. Biol. Chem., 1997, 272: 4269-4275).

A consensually identified epitope of myelin basic protein (residues 90-102) embraces a unique and highly conserved hexapeptide string containing four prolines, three of which are contiguous in the alignment of TPRTPPPSQ (SEQ. ID. NO. 1). The triple proline segment, residues 99-101, has been regarded as a keystone element supporting the overall architecture of the molecule. Aze substitution for prolines in the region could severely alter protein conformation and exert tectonic stress because of the unique torsion angles and steric constraints of the proline analogue. (Tsai et al., Synthesis and peptide bond orientation in tetrapeptides containing L-azetidine-2-carboxylic acid and L-proline. Biopolymers, 1990, 30: 1039-1049). Such effects may influence reciprocal nesting with adjacent molecules. Additional details regarding the implications of Aze misincorporation in myelin basic protein and its putative role in multiple sclerosis is discussed in greater detail below.

Proline Substitution and Multiple Sclerosis

Until recently there were only two known natural sources of Aze, sugar beets (*Beta vulgaris*) and Liliaceae. Since humans do not consume sugar beets or lilies as food, Fowden's observations did not raise concern about human disease, although Aze was subsequently shown to be highly toxic, teratogenic, and capable of being misincorporated into the proteins of numerous species, including our own. The compound has recently been identified in garden or red beets, the vegetable that makes its way to the human table. In some regions garden beets are a mainstay of the diet. The concern about Aze goes beyond table beets, and includes sugar beets as well. Their by-products may be inundating regions of Europe and North America. It is difficult to determine with accuracy the precise quantities, but it is likely that the European Union produces about 25 million tons of sugar annually. This amount requires the yearly harvesting of about 100 million tons of sugar beets containing about 70,000 kilograms of Aze. Beets belong to the goosefoot family (Chenopodiaceae). Aze has not been found thus far in the two other members of this family, spinach (*Spinacia oleracea*) and Swiss chard (*Beta vulgaris* var. *flavescens*). There may be other natural vehicles that produce or disperse Aze; further studies are needed to determine its distribution in nature.

Sugar is extracted from shredded beets by boiling, evaporation, and crystallization. The residue is processed into beet molasses and then into various protein-containing pulp by-products, which are fed to cattle, sheep, and pigs. In this way the highly noxious nonprotein amino acid, Aze, can enter the food chain, including dairy products.

The clinical expression of many autoimmune disorders requires the presence of an environmental agent exerting its effects on genetically susceptible individuals. The long latency period characteristic of most autoimmune diseases presents a confounding factor. In the case of multiple sclerosis, the risk of developing the disease appears to be strongly influenced by the location of the individual's residence during childhood, a factor that may outweigh the importance of genetic predisposition.

There is a tight fit between the worldwide prevalence of multiple sclerosis and the geography of beet agriculture. This correlation goes beyond the occurrence of multiple sclerosis in higher latitudes. Beets share this cartography, but their adaptability allows them to flourish under more temperate conditions, such as those of the Mediterranean littoral. In each high-prevalence cluster of cases of multiple sclerosis, beets are a principal commodity or dietary staple. This specification applies to Sardinia, the Orkney Islands, the Middle East, Finland, the Faroe Islands, Alberta, and the Tokachi province in Hokkaido. Tokachi province has the highest rate of multiple sclerosis reported to date in Orientals. Although its population constitutes only 0.3% that of Japan, it produces 45% of Japan's sugar beets. Alberta is the Canadian epicenter for both sugar beet agriculture and for the prevalence of multiple sclerosis.

Alberta is significant in another way. It was in this province that an outbreak of enzootic ataxia (swayback) occurred in newborn lambs; the neurological manifestations included prostration, head shaking, ataxia, trembling, swaying of the hind quarters and collapse of the posterior trunk. Pathologic studies revealed widespread abnormalities of myelin. A salient observation led to the report that the ewes and the affected offspring had been fed sugar beet silage during pregnancy, lambing, and lactation. This observation is consistent with the concept that proline replacement by Aze, derived from consumption of beets, may cause changes in the topology and charge distribution of myelin. Such alterations can result in dysgenesis, dysfunction, local inflammation, and subsequent autoimmune responses. They also suggest that lambs may be a suitable animal model for the study of multiple sclerosis, including investigations of the effects of feeding Aze. Swayback has been attributed to viruses, copper deficiency, and autoimmune responses to myelin degeneration, but none of these proposals has been validated. Diseases resembling swayback have been reported in various forms of wildlife. The grazing habits of such animals may reveal new plant sources of Aze, although fodder beets are widely available.

There may be other plants or natural vehicles that produce or disperse Aze. Further studies are needed to determine its distribution in nature. In wheat, Aze is a central molecule in a putative methionine cycling biosynthetic pathway involved in the uptake of insoluble iron from soil. Thus, wheat and other gramineous plants may have an endogenous source of Aze, as well as environmental exposure to it. The proline-rich wheat protein, gluten, implicated in celiac disease, is a vulnerable target for Aze misincorporation. The allergenic peptide of gluten contains 30 amino acids, of which 8 are prolines.

The putative role of Aze should be interpreted in the light of the well-established role of immunogenetic susceptibility. In the present context, predisposition to disease could be owing to many factors, including, among others, dysfunction of tRNA, ribosomes or miRNA, the replacement, positioning or the disposition of misassembled proteins, or abnormalities of the immune system.

There are molecular as well as geographic hot spots for multiple sclerosis. In regard to myelin basic protein, proline-rich sequences are sites of vulnerability, loci in which Aze substitution for proline may result in disease-causing epitope formation. A triple proline chain may be a structure especially vulnerable to deformation. As discussed above, the unique torsion angles of Aze peptide bonds may alter the contour of molecules in which the compound is misincorporated. As will be presented in greater detail below, aspects of the present disclosure provide methods and systems for testing for Aze in host proteins and testing for host antigenicity to host peptides containing Aze, which could be implicated in disorders including, but not limited to, various auto-immune disorders including multiple sclerosis. Due to the putative role of Aze in a variety of disorders, such as those discussed above, it is important to limit the amount of Aze consumed by humans and animals, particularly animals that provide sources of food consumable by humans. Therefore, tests, such as those described below are needed for detecting the presence of Aze in food, food precursors, and food byproducts.

Tests for the Presence of Azetidine-2-Carboxylic Acid

Tests for the detection of azetidine-2-carboxylic acid in tissues, lesions, foods and/or food byproducts, among other materials, include, but are not limited to, those intended for use by trained personnel working in laboratories, and those intended for use by producers, distributors, sales personnel or consumers who wish to test products for the presence of azetidine-2-carboxylic acid at the point of production, distribution, sales, consumption or exposure.

The present disclosure provides methods and systems for detecting Aze in food consumable by humans or animals, such as, but not limited to, beets and beet byproducts. In particular, methods of detecting Aze in food produced from an animal (e.g., livestock) fed materials containing Aze (e.g. sugar beet byproducts) are provided. When such animals are fed Aze-containing materials, that Aze may be passed on to humans or other animals fed food produced from such animals, such as eggs, milk, beef, pork, and poultry. Furthermore, additional embodiments include methods of detecting Aze in yeast, since yeast is produced using sugar beet byproducts (e.g., molasses). Any food, food precursor, or food byproduct suspected of being linked to Aze can be tested according to the methods and systems of the present disclosure.

Some exemplary methods of the present disclosure for testing for the presence of Aze in food or host samples (e.g., tissues, sera) include using spectroscopy and chromatography, and other chemical analysis techniques known to those of skill in the art, now known or to be developed. Exemplary methods of using spectroscopy and chromatography for detecting Aze in food are provided in Example 1 below.

Tests for detecting Aze provided in the present disclosure can also be based on methods such as antibody recognition, chromatography, and mass spectrometry. In one embodiment, a test for the presence of Aze in a sample includes an antibody to Aze. In one embodiment of the present disclosure, a kit for testing for the presence of Aze includes an antibody to Aze bound to a solid support (e.g., polystyrene beads in the form of latex) for use in a standard latex agglutination test (LAT) for Aze. When contacted with a sample containing antigenic material (e.g., a sample containing Aze), the beads will agglomerate, causing a change in appearance that can be detected. Other diagnostic assays, known to those of skill in the art, can also be used with Aze antibodies for the detection of Aze. Such assays include, but are not limited to, enzyme immunoassays (EIA), enzyme-linked immunoassays (ELISA), and radioimmunoassays. Such assays are performed using standard methods known to those of skill in the art, such as described in U.S. Pat. Nos. 5,225,331, 5,223,410, 5,741,652, and 6,510,023, which are hereby incorporated by reference. Antibodies to Aze for use in such assays and assay kits can be produced by methods known to those of skill in the art.

In one embodiment, polyclonal antibodies to Aze can be produced by inoculating a host (e.g., a rabbit, goat, mouse, and the like) with a composition including Aze; testing for the presence, at a desired level, of antibodies specific for Aze; collecting sera or other body fluids (e.g., cerebrospinal fluid (CSF)) containing Aze antibody from the inoculated host; obtaining purified polyclonal antibodies to Aze by passing the sera over a column including bound Aze; and eluting the purified anti-Aze antibodies. Such methods are known to those of skill in the art, and are described for example in U.S. Pat. No. 5,610,023, which is hereby incorporated by reference.

Other methods, known to those of skill in the art, for producing monoclonal and/or polyclonal antibodies can be used to produce anti-Aze antibodies for use in testing for the presence of Aze in a sample of interest. Such methods are known to those of skill in the art, and are described for example in U.S. Pat. Nos. 5,225,331, 5,223,410, 5,741,652, and 6,510,023, which are hereby incorporated by reference. A sample of interest to be used in the assays described above may include samples from an organism suspected of containing Aze, such as tissue or fluid samples, or the sample may include a food or food-product suspected of containing Aze.

The present disclosure also includes methods of testing for the presence of Aze using Aze-toxicity screens in bacterial strains sensitive to Aze (e.g., Aze-susceptible strains of *E. coli*), by methods known to those of skill in the art. Also included in the present disclosure are methods for detecting/testing for Aze using tests based on standard analytic chemistry, such as screening for Aze based on differential water/ethanol solubility and optical activity, based on known properties of Aze, such as those presented for Aze in the Merck Index, 1996, 12$^{th}$ Ed, p. 156, cmpd. 940, which is hereby incorporated by reference herein.

Genetic Modification of Beets or Other Foods Containing Azetidine-2-Carboxylic Acid The present disclosure also includes methods of genetic modification to eliminate and/or inhibit the synthesis by a plant of azetidine-2-carboxylic acid. Such methods are well-known in the art. For example, an exemplary embodiment includes a genetically modified beet having a knock-out mutation for a gene responsible for and/or required for the synthesis of Aze. The beet genome has been studied by those of skill in the art; the sequences of many beet genes are known and can be found for instance on the NCBI database available at Gen Bank, http://www.ncbi.nlm.nih.gov. The beet genome has also been discussed and described in detail in references such as the following, which are hereby incorporated by reference: Barzen E, Melchelke W, Ritter E, Schulte-Kappert E, Salamini F (1995). An extended map of the sugarbeet genome containing RFLP and RAPD loci. Theor Appl Genet 90:189-193; McGrath, J. M. (2005) Genomics in Genetic Improvement. In: Biancardi, E., Campbell, L., Skaracis, G. N., de Biaggi, M. (eds) Genetics and Breeding of Sugarbeet. Science Publishers, Inc., New Hampshire, USA (in press), 221-234; Biancardi E, Campbell L, Skaracis G N, De Biaggi M (2005) Genetics and Breeding of Sugar Beet. Science Publishers, Enfield N.H., USA; Pillen K, Steinrücken G, Herrmann R G, Jung C (1993) An extended linkage map of sugar beet (*Beta vulgaris* L.) including nine putative lethal genes and the restorer gene X. Plant Breed 111:265-272; McGrath, J. M. 2003. Alphabet Soup for Beets: Status of ESTs, BACs, RILs and other genomic sundries. ASSBT Proceedings (in press). The gene or genes responsible for the synthesis of Aze, or directly or indirectly related to Aze activity, can be identified and isolated by methods known to those of skill in the art.

For instance, the molecule S-adenyl methionine (AdoMet) is likely the precursor to Aze in beets and other organisms. This compound is a primary methyl donor in a large number of methyltransferase reactions, including one involving the synthesis of a nonprotein amino acid (homocysteine) in mammals. The nucleotide sequence of beet genes for AdoMet is known (NCBI AB221009 and AB221010). Thus, the enzyme responsible for the conversion of AdoMet to Aze presents a target for genetic manipulation to eliminate Aze production in beets. For example, an embodiment of the present disclosure includes a beet or beet cell that is genetically modified to reduce and/or substantially eliminate the activity of the AdoMet-Aze conversion enzyme (e.g., a genetically modified beet having a knock-out gene for the AdoMet-Aze enzyme). The present disclosure also includes other methods, known to those of skill in the art for modulating the activity of such an enzyme, e.g., through the use of agonists, antagonists, and/or genetic manipulation. Additional information about biologic Aze pathways is described in Fowden, L., Azetidine-2-carboxylic acid: a new cyclic amino acid occurring in plants. Biochem J 1956; 64:323-32 (see, e.g., p. 325) and in Ma J F., J. Biol. Chem. 1996; 270:16549-54, which are hereby incorporated by reference herein.

Methods for genetically modifying plants, and in particular beets, and for producing transgenic plants are known to those of skill in the art. Methods for producing genetically modified beets are described, for example, in U.S. Pat. Nos. 5,739,082, 5,866,790, 6,204,436, 6,531,649, 6,774,085, and 6,956,149, which are hereby incorporated by reference herein.

The present disclosure also includes other plants that include Aze, such as wheat, that have been genetically modified to remove and/or render inoperable (e.g., a knock-out mutation) a gene responsible for the synthesis and/or presence of Aze in the plant. Wheat has been found in certain situations (e.g., iron starvation) to produce Aze as an intermediate. For instance, in iron deficient environments, the wheat plant produces an increased concentration of iron-chelating molecules, and an intermediate of this process is Aze. The production of Aze could then lead to incorporation of Aze into wheat proteins, such as for example, gluten. Gluten is a known modulator of auto-immune diseases, including, but not limited to, those of the gastrointestinal organs, including celiac disease. The gluten molecule includes a 30 amino acid peptide, 8 of which (¼ of the peptide) are proline. Thus, if Aze (produced endogenously by the wheat plant, such as resulting from iron deficient conditions, or taken up by the wheat plant from the environment, e.g. the soil) finds its way into the gluten peptide, this could be a factor in the incidence of auto-immune disease and certain types of diabetes (which involve immune responses known to be induced by this gluten peptide sequence).

Like wheat, other crop plants may also incorporate Aze under certain environmental conditions. For instance, during dehydration, excessive local salinity, or excessively high ambient temperatures many plants accumulate proline because free proline provides a protection against osmotic stress. Proline is stored by many plants in amounts that exceed any other free amino acid. This is because of the unique chemistry of proline. Proline is referred to by plant biologists as a "compatible osmolyte." No other amino acids are known to belong to this category of compound. Compatible osmolytes are highly water soluble and uncharged at neutral pH. Even at high concentration they do not perturb the conformation of large molecules. They are excluded from the hydration sphere of proteins and in this way they protect the folded structure of a protein.

The significance of proline as such a compatible osmolyte means that plants may accumulate proline during times of environmental stress. In addition to endogenous synthesis of the amino acid, the plants may take up increased amounts of proline from their environment. Thus, they may also take up environmental Aze at the same time. Plants such as wheat, corn, rice, and the like may acquire excessive Aze at such times and misincorporate it into their proteins. This can be tested by various methods, such as radio-isotope labeling, known to those of skill in the art. Thus, during such environmental stress, plants in the local biosphere of sugar beets (e.g., due to proximity or crop rotation with sugar beets) may be especially vulnerable to such misincorporation, and, in the process, pass the Aze up the food chain, eventually to humans. Additional information about plant accumulation of compounds under stress can be found in Stewart G R, Larher F. 1980, Accumulation of amino acids and related compounds in relation to environmental stress; The Biochemistry of PLants. (B J Miflin ed), Vol 5, Academic Press, New York, pp. 609-635; and Rhoded D, Handas, Bressan R A 1986, Metabolic changes associated with adaptation of plant cells to water stress, Plant Physiol 82:890-903, which are all incorporated by reference herein.

Thus, the present disclosure also includes methods of producing genetically modified wheat that does not produce Aze, as well as methods for processing wheat to remove any residual Aze. Methods for producing genetically modified plants, such as wheat, are known to those of skill in the art, and are described in for example, U.S. Pat. Nos. 5,405,765, 5,631,152, 5,973,225, and 6,153,812, which are hereby incorporated by reference.

Techniques for transforming a wide variety of plant cells are well known in the art and described in the technical and scientific literature. See, for example, Weising et al. (1988) Ann. Rev. Genet. 22:421-477. To express an exogenous gene in a plant cell, the gene can be combined with transcriptional and translational initiation regulatory sequences that direct the transcription of the gene and translation of the encoded protein in the plant cell.

Non-essential nucleotides could be placed at the 5' and/or 3' end of the fragments (or the full-length gene of interest) without affecting the functional properties of the fragment or molecule. For example, the nucleotides encoding the protein may be conjugated to a signal or transit (or leader) sequence at the N-terminal end (for example) of the protein that co-translationally or post-translationally directs transfer of the protein. The nucleotide sequence may also be altered so that the encoded protein is conjugated to a linker or other sequence for ease of synthesis, purification, or identification of the protein.

For example, for over-expression, a constitutive plant promoter may be employed. A "constitutive" promoter is active under most environmental conditions and states of cell differentiation. Examples of constitutive promoters include the cauliflower mosaic virus (CaMV) 35S transcription initiation region, the 1'- or 2'-promoter derived from T-DNA of *Agrobacterium tumafaciens*, the ACT11 and Cat3 promoters from *Arabidopsis* (Huang et al. (1996) Plant Mol. Biol. 33:125-139 and Zhong et al. (1996) Mol. Gen. Genet. 251:196-203), the stearoyl-acyl carrier protein desaturase gene promoter from *Brassica napus* (Solocombe et al. (1994) Plant Physiol. 104: 1167-1176), and the GPc 1 and Gpc2 promoters from maize (Martinez et al. (1989) J. Mol. Biol. 208:551-565 and Manjunath et al. (1997) Plant Mol. Biol. 33:97-112).

Alternatively, a plant promoter may be employed to direct expression of the gene of interest (e.g., an Aze acetyltransferase gene) in a specific cell type (e.g., tissue-specific promoters) or under more precise environmental or developmental control (e.g., inducible promoters). Examples of such promoters include the root-specific ANR1 promoter (Zhang and Forde (1998) Science 279:407) and the photosynthetic organ-specific RBCS promoter (Khoudi et al. (1997) Gene 197:343).

For proper polypeptide expression, a polyadenylation region at the 3'-end of the coding region is preferably included. The polyadenylation region can be derived from the natural gene, from a variety of other plant genes, or from T-DNA.

A marker gene can also be included to confer a selectable phenotype on plant cells. For example, the marker gene may encode a protein that confers biocide resistance, antibiotic resistance (e.g., resistance to kanamycin, G418, bleomycin, hygromycin), or herbicide resistance (e.g., resistance to chlorosulfuron or Basta).

A recombinant nucleic acid that encodes an exogenous gene of interest (e.g., an Aze knock-out gene or an Aze acetyltransferase gene (see discussion of Aze acetyltransferases, below)) may be introduced into the genome of a desired plant host cell by a variety of conventional techniques. The recombinant nucleic acid along with one or more of the additional elements described above (e.g., promoter, marker gene, etc.) may be incorporated into a plasmid for use in introducing the recombinant nucleic acid to the plant cell. Various plasmids and methods of use are known in the art and described in the literature.

Then, other techniques may be employed for introducing a plasmid or naked recombinant nucleic acid into the plant cell to be transformed. For example, the recombinant nucleic acid may be introduced directly into the genomic DNA of a plant cell using techniques such as electroporation and microinjection of plant cell protoplasts, or the recombinant nucleic acid can be introduced directly to plant tissue using ballistic methods, such as DNA particle bombardment.

Microinjection techniques are known in the art and well described in the scientific and patent literature. The introduction of a recombinant nucleic acid using polyethylene glycol precipitation is described in Paszkowski et al. (1984) EMBO J. 3:2717-2722. Electroporation techniques are described in Fromm et al. (1985) Proc. Natl. Acad. Sci. USA 82:5824. Ballistic transformation techniques are described in Klein et al. (1987) Nature 327:70-73.

The recombinant nucleic acid may also be combined with suitable T-DNA flanking regions and introduced into a conventional *Agrobacterium tumefaciens* host vector. The virulence functions of the *Agrobacterium tumefaciens* host will direct the insertion of the exogenous gene and adjacent marker into the plant cell DNA when the cell is infected by the bacteria. *Agrobacterium tumefaciens*-mediated transformation techniques, including disarming and use of binary vectors, are well described in the scientific literature. See, for example, Horsch et al. (1984) Science 233:496-498; Fraley et al. (1983) Proc. Natl. Acad. Sci. USA 80:4803; and Gene Transfer to Plants, Potrykus, ed., Springer-Verlag, Berlin, 1995.

A further method for introduction of the plasmid into a plant cell is by transformation of plant cell protoplasts (stable or transient). Plant protoplasts are enclosed only by a plasma membrane and will therefore take up macromolecules like exogenous DNA. These engineered protoplasts can be capable of regenerating whole plants. Suitable methods for introducing exogenous DNA into plant cell protoplasts include electroporation and polyethylene glycol (PEG) transformation. As used throughout this application, electroporation is a transformation method in which, generally, a high concentration of plasmid DNA (containing exogenous DNA) is added to a suspension of host cell protoplasts and the mixture shocked with an electrical field of 200 to 600 V/cm. Following electroporation, transformed cells are identified by growth on appropriate medium containing a selective agent.

The presence and copy number of the exogenous gene in a transgenic plant can be determined using methods well known in the art, e.g., Southern blotting analysis. Expression of the exogenous gene in a transgenic plant may be confirmed by detecting the exogenous mRNA or protein in the transgenic plant. Methods for detecting and quantifying mRNA or proteins are well known in the art.

Transformed plant cells that are derived by any of the above transformation techniques, or other techniques now known or later developed, can be cultured to regenerate a whole plant. Such regeneration techniques rely on manipulation of certain phytohormones in a tissue culture growth medium, typically relying on a biocide or herbicide marker that has been introduced together with the exogenous gene. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. (1987) Ann. Rev. Plant Phys. 38:467-486. Once the exogenous gene has been confirmed to be stably incorporated in the genome of a transgenic plant, it can be introduced into other plants by sexual crossing. Any of a number of standard breeding techniques can be used, depending upon the species to be crossed.

The present disclosure also includes methods of generating non-Aze generating plant varieties by selective breeding techniques, as opposed to through genetic engineering. Breeding techniques for selecting for desired mutations (e.g., a beet mutant lacking the ability to produce and/or incorporate Aze) are known to those of skill in the art and are currently in use for producing beets with increased sucrose production and decreased disease susceptibility. Such methods can be used to select for plants that lack Aze production and/or incorporation capabilities.

Methods and Compositions for Detoxifying/Inactivating Aze

The present disclosure also includes methods and compositions for detoxifying Aze and/or Aze-containing materials and/or products. Such methods include genetic modification of Aze without production of an Aze knock-out as described above. Such methods include use of the gene (homolog thereof, functional variant thereof, or fragment thereof) and/or protein (homolog thereof, functional variant thereof, or fragment thereof) for an Aze acetyltransferase (e.g., the acetyltransferase MPR1 and MPR2 from *Saccharomyces cervisiae*, which confers resistance to Aze by acetylating it, such as described in Shichiri, M. et al., A Novel Acetyltransferase Found in *Saccharomyces cervisiae* 1278b That Detoxifies a Proline Analogue, Azetidine-2-carboxylic Acid, *J. Biol. Chem.*, Vol. 276, 45:41998-42002 (2001) and in Kimura, Y. et al., Polymorphism of the MPR1 Gene Required for Toxic Proline Analogue Resistance in the *Saccharomyces cervisiae* Complex Species, Yeast, Vol. 19, 16: 1437-1445 (2002), which are hereby incorporated by reference herein).

Methods of the present disclosure include, but are not limited to, creating transgenic beets, as described above, that have been engineered, by methods known to those of skill in the art (and as described above), to include a gene (homolog thereof, variant thereof, or fragment thereof) for an Aze acetyltransferase (e.g., the Aze acetyltransferase MPR1 and MPR2 from *Saccharomyces cervisiae*, described above). The present disclosure also includes genetically modified beets, wheat, or other Aze-containing plants, that include the gene for an Aze acetyltransferase. The nucleotide sequence for the yeast Aze acetyltransferases MPR1 and MPR2 are known (NCBI AB084520 and AB083128).

Methods of the present disclosure also include detoxifying materials containing Aze by contacting such materials with a composition including an Aze acetyltransferase. Such methods include inactivating Aze in food consumable by humans or animals by contacting the food with an effective amount of an Aze acetyltransferase that is effective to inactivate Aze by acetylation, such as the Aze acetyltransferase MPR1 and MPR2 from *Saccharomyces cervisiae*, described above. As used herein, the term "inactivate" with respect to Aze, refers to a method or composition capable of altering the structure of Aze to prevent it from being misincorporated into host proteins, or otherwise rendering it incapable of incorporation into host proteins. For instance, an example of "inactivating" Aze would be acetylation by an Aze acetyltransferase, or the physical disruption of the Aze ring structure by heat or other method.

Another embodiment of a method of inactivating Aze in food consumable by humans or animals includes heating the food or other material (e.g., a food precursor, ingredient, or food processing byproduct) containing Aze to a temperature effective to rupture the ring-structure of Aze. There is considerable ring strain in the Aze molecule because of the 90 degree bond angles of the four-membered ring. Such rings are susceptible to rupture and molecular decomposition by exposure to high temperature (or very low pH, etc.). The temperatures of the boiling/distillation process (e.g., about 100 degrees C.) are not believed to be effective at inactivating Aze, as Aze was found to be present in pasteurized milk (Example 1) as well as in animal feed containing beet byproducts of the sugar distillation process. Thus, the food or other Aze-containing material is desirably heated to a temperature above about 100 degrees C. The temperature and the duration of heating should desirably be limited to levels below which carcinogenic heterocyclic amines may form as a result of amino acids interacting with creatine (plants may contain low levels of creatine). In cooking meat, there is a three-fold increase in heterocyclic amines when the temperature is increased from about 200 degrees C. to 250 degrees C. Therefore, it is desirable, although not required, to keep the inactivation heating temperature below about 200 degrees C. It may be the case that creatine is present in such low concentrations that heterocyclic amine formation from processing of vegetation is of trivial consequence, in which case temperatures over about 200-250 degrees C. would be more acceptable. In exemplary embodiments, Aze is inactivated by heating food or other Aze-containing materials, in particular beet byproducts, to a temperature of about 100 to 200 degrees C. In some embodiments, the temperature is from about 115 to 180 degrees C. It is believed that heating such materials to this temperature range will provide an opportunity to destroy Aze in the effluent residue after sugar crystallization. Such an approach to Aze decomposition may be one means of destroying Aze without causing substantial stress on sugar beet enterprises.

Other potential sources of anti-Aze compounds (such as Aze inhibitors, or compounds that otherwise interfere with Aze activity) that may be used to inactivate Aze include organisms known to prey on beets, including but not limited to, maggots, cutworms, wireworms, leaf beetles, grasshoppers, aphids, webworms, leaf miners, and nematodes.

Removal of Aze from the Food Chain

The present disclosure also includes methods of removing Aze from the food chain. For example, one embodiment includes removing Aze from wheat, sugar beets and/or sugar beet by-products (e.g., sugar beet molasses or beet pulp that is fed to livestock animals) during processing. It is important not only to remove Aze from beet products fed to animals but also from byproducts discarded as waste, since it is important to remove Aze-containing material from the biosphere.

Methods of removing Aze from beet and other Aze-containing plants and products include, but are not limited to, acetylating, de-carboxylating and/or de-aminating the Aze and/or Aze-containing proteins and/or peptides. The acetylation of Aze can be accomplished by contacting Aze-containing materials with a composition including an Aze acetyltransferase, such as described above. The present disclosure includes both methods of inactivating Aze via Aze acetyltransferases and compositions containing an effective amount of an Aze acetyltransferase.

In other embodiments, the Aze-containing materials may be de-toxified of Aze by de-carboxylation or de-amination, which splits the Aze ring structure, so that it will no longer be incorporated in place of proline in proteins. This can be accomplished by processes known to those of skill in the art, such as by contacting materials and/or samples containing Aze with chemicals or to processes known to accomplish the desired de-carboxylation or de-amination of the Aze ring-structure.

Other embodiments of removing Aze from the food chain include the methods of inactivating Aze in food consumable by animals or humans by the methods described above, including heating the Aze-containing food to temperatures effective to rupture the ring-structure of Aze.

In addition it should be mentioned that an additional method of removing Aze from at least some portions of the food chain, particularly Aze acquired by grazing animals through consumption of beets and/or beet byproducts, is to make sure that the livestock consume only the non-root portions of the beet plant. For instance, the leaves and stems of beets (both garden beets and sugar beets) are free from Aze; it is only the root portion that contains Aze. Aside from the beet byproducts from sugar beet processing that are incorporated into some animal feeds or directly fed to animals, many livestock animals are also fed the leaves, stem, and upper root portion of beets that is leftover from beet harvesting. When harvesting beets, generally the stems, leaves, and upper third of the root are removed from the remainder of the beet root. Thus, this represents another source of Aze fed to livestock. However, if harvesting methods were altered to make sure that none (or a minimal amount) of the root portion was included in the beet leaves and stems fed to livestock, this would remove a source of Aze from the food chain.

Tests to Determine Susceptibility to Disease Caused by Azetidine-2-Carboxylic Acid The present disclosure also includes methods and compositions for determining the susceptibility of a host to diseases or conditions (such as autoimmune disorders) mediated by and/or associated with Aze.

Such tests detect increased susceptibility to deleterious effects of azetidine-2-carboxylic acid. Such tests can address immune mechanisms, such as HLA or related immunologic markers. (Online Mendelian Inheritance in Man, OMIM™. Johns Hopkins University, Baltimore, Md., MIM Number 126200: Feb. 9, 2005).

Other tests detect impaired fidelity in translation mechanisms, involving misincorporation of a non-protein amino acid in place of a protein amino acid or the inappropriate insertion of a protein amino acid in place of another. Such tests identify abnormalities involving tRNA, tRNA synthetases, and ribosomal constituents.

Such tests can include tests to detect the presence of Aze in host proteins (such as by using the tests and kits described above) as well as tests to detect/determine the presence of antibodies to Aze-containing antigens that may be the cause and or a mediator of disease (such as described below). Various host organisms can be tested, from cows, goats, and sheep, to humans.

Lambs present a good model for the investigation of the effects of Aze, due to the presence of the disorder enzootic ataxia (swayback), as discussed above, which may be linked to an autoimmune response to myelin degeneration, which may be linked to Aze incorporation in myelin.

Tests to Detect the Presence of Antibodies or Other Cellular Immune Responses to Antigens Containing Azetidine-2-Carboxylic Acid The present disclosure includes methods and compositions for determining antigens that mediate autoimmune response in patients with auto-immune disease. Due to the strong links between Aze and the prevalence of autoimmune diseases, it is believed that such antigens will include Aze.

Since not every person or host exposed to Aze will contract an autoimmune disease, the disease also likely involves a genetic component. The genetic component may include, for instance, a break-down in the cellular mechanisms for correcting mis-incorporation of Aze (and/or other non-protein amino acids) or an immune system particularly sensitive to the presence of non-protein amino acids, such as Aze, in host proteins. Thus, the present disclosure includes methods for detecting Aze in host polypeptides as well as detecting an immune response to antigens containing Aze (e.g., the presence of antibodies to peptides, such as host peptides or portions thereof, containing Aze).

One embodiment includes detecting Aze in host polypeptides to confirm misincorporation of Aze in host polypeptides. The host may be a healthy host or a host with a disorder with a putative association with Aze misincorporation, such as multiple sclerosis. Aze present in host proteins may be detected in a number of ways, such as by spectroscopy, as demonstrated in Example 2, where peak shifts can be seen representing the presence of Aze instead of proline (see FIG. 4). In other methods, antibodies to Aze can be used to detect polypeptides containing Aze in a host sample. An exemplary embodiment includes obtaining a sample from a host, where the sample includes host polypeptides and contacting the host sample with a composition including at least one anti-Aze antibody, where the at least one anti-Aze antibody recognizes at least one host polypeptide having Aze in place of proline in the polypeptide sequence.

The present disclosure also includes methods of detecting anti-Aze antibodies. Such antibodies can then be used for screening for Aze-containing antigens in a host and for diagnosing disorders associated with Aze misincorporation by recognizing the Aze containing antigen in the host. Methods of detecting anti-Aze antibodies can also be used to diagnose disorders associated with Aze by detecting the anti-Aze antibodies in a host sample.

One embodiment of the present disclosure includes detecting antibodies to Aze in a host. This provides the ability to determine if certain hosts (e.g., hosts with certain disorders, such as multiple sclerosis or other auto-immune disorders, among others) harbor anti-Aze antibodies that can serve as an indicator of disease state, thereby leading to a diagnostic tool. In an embodiment of a method of detecting antibodies in a host, a host sample is provided that contains host antibodies (e.g., blood, saliva, urine, sera, cerebro-spinal fluid, etc.). At least one peptide (or a mixture of peptides) is provided, where the peptide(s) is a derivative of a wild-type peptide having at least one proline residue replace by Aze (e.g., SEQ. ID. NOS. 2-8). In a particular example, the host has multiple sclerosis and the peptide is a portion of the sequence of myelin basic protein having proline residues with one or more proline residues replaced by Aze. The host sample is contacted with the peptide(s) and examined for any binding between the peptide(s) and any antibody from the host sample, where binding indicates the presence of an antibody to the Aze containing peptide. Methods known to those of skill in the art can be used to detect binding, such as by using well-known reporter molecule systems (e.g., fluorescent dyes, and other detectable labels).

In particular embodiments the host has or is suspected of having an autoimmune disorder, and samples from the host are tested for affinity to Aze and/or Aze containing antigens. Such affinity tests are known to those of skill in the art. For instance, Aze and/or Aze-containing antigens can be bound to a solid support (e.g., in a column), a sample containing sera or CSF (cerebro-spinal fluid) from a host with an autoimmune disorder (such as multiple sclerosis) can be contacted with the column, the column can be washed, and then any bound antibody can be eluted and analyzed.

The present disclosure also includes methods of screening a library of peptides containing Aze for antigenicity. Such methods include detecting antibodies by providing a library of peptides having Aze in place of at least one proline residue. The library of peptides is contacted with a composition that includes antibodies. The composition may include a known antibody or a known mixture of antibodies, or the composition may include unknown antibodies. Furthermore, the sample may be a sample from a host that contains host antibodies (e.g., blood, serum, saliva, urine, cerebro-spinal fluid, or other sample). Then the antibody library and sample are examined to determine if any binding has occurred between the peptides and an antibody present in the antibody composition, where binding indicates the presence of an antibody to an Aze containing peptide in the library. In exemplary embodiments, the library of peptides includes one or more peptides selected from the peptides of SEQ. ID. NOS. 2-8, described herein. The library may include peptides having partial sequences of one or more of the following human proteins, where the wild-type sequence has at least one proline residue that has been replaced by Aze: myelin basic protein, collagen, hypoxia-inducible factor, profilins, ion channel proteins, vesicular glutamate transporters, and hemoglobins.

Binding between the Aze-containing peptides in the library and an antibody in the antibody-containing composition can be detected by any number of methods known to those of skill in the art, such as by the use of fluorescent labels or other detectable labels. Library screening may be performed on a solid support such as a column or an array. An array format may be particularly suitable to screening a large library of potential peptide antigens.

In an embodiment, a library of Aze-containing antigens (e.g., short Aze-containing peptides) can be labeled with a signal molecule (e.g., a fluorescent dye molecule). A solution containing a sample from a host with an autoimmune disorder can then be contacted with a composition containing one or more labeled Aze-containing antigens, and association of one or more of the antigens with an Aze antibody in the host sample can be determined by detection of the signal molecule.

In particular, the present disclosure includes methods including providing a library of Aze-containing peptides and testing said peptides for antigenicity. In preferred embodiments, the Aze-containing peptides are nonamers (peptides having 9 amino acids, at least one of which is Aze). This is because in the immune system, antigens presented by the host cells' MHC complex to host immune cells (e.g., B and T cells and macrophages) are generally 9 amino acids in length. Thus, an exemplary library would contain several nonamers having Aze incorporated in place of proline. The peptides (e.g., potential antigens) can be chemically synthesized or produced in biologic systems by methods known to those of skill in the art.

In particularly preferred embodiments, the library of nonamers is prepared from proteins and/or peptides believed to be implicated in autoimmune diseases, such as, but not limited to, myelin, collagen, and elastin. Preferably such proteins or peptides also have a long half-life and are proline rich. It is known that myelin, a neuronal protein, is attacked by the immune system of patients with multiple sclerosis, but it is not known if this attack is mediated by the myelin itself or another protein. The present disclosure provides libraries of nonamers made of 9 amino acid length fragments of the myelin basic protein, in which the prolines are substituted with Aze. Of particular interest, is the sequence spanning amino acids 91-104 of the myelin basic protein, in particular the nonamer that represents amino acids 95 to 103 of wild type myelin basic protein and has the sequence TPRTPPPSQ (SEQ. ID. NO. 1). For instance, exemplary nonamers would have one or more of the prolines of the above sequence replaced by Aze (Az). Exemplary derivatives from this nonamer include, but are not limited to, the following sequences: TAzRTPPPSQ (SEQ. ID. NO. 2), TPRTAzAzAzSQ (SEQ. ID. NO. 3), TPRTAzAzPSQ (SEQ. ID. NO. 7), and TPRTAz-PPSQ (SEQ. ID. NO. 8), among others, as provided below in Table 1.

As discussed above, collagen contains a very high concentration of proline (nearly 15% of the amino acids in collagen are proline, with proline making up nearly every $3^{rd}$ amino acid in some portions of the sequence); thus, it also represents a particularly good candidate for generating Aze-containing antigen libraries. With the high concentration of proline, a number of potential nonamer fragments of collagen, having Aze incorporated in place of one or more prolines, could be used as potential antigens in auto-immune disorders.

The peptide libraries are then tested for antigenicity against samples derived from patients with auto-immune diseases, such as multiple sclerosis, such as by methods described above, and other methods known to those of skill in the art (such as those that can be used to screen for an affinity between members of the peptide library of potential antigens and antibodies present in hosts with auto-immune diseases).

Thus, the present disclosure includes the antigens and antigen libraries described above, as well as the methods described above for screening for antigenicity to antibodies of patients with auto-immune disorder. Positive antigens (e.g., antigens screening positive for antigenicity in patients with auto-immune disorder, and particularly antigens that are positively identified as a specific target in one or more auto-immune disorders) can then be used to screen other patients/hosts for the presence of such antibodies. The methods can be used to screen patients/hosts for the existence of or a predisposition to various auto-immune diseases.

Samples to be used in such screening tests include, but are not limited to, tissues, lesions, blood, blood components (including cells), urine, cerebrospinal fluid, and other biologic fluids or samples from humans or other animals.

The present disclosure also includes the Aze-containing antigens themselves. Such antigens (e.g., Aze-containing peptides) can be used as diagnostic and research tools as described above, to detect anti-Aze antibodies and aid in the diagnosis of disorders. Exemplary peptides include polypeptides having a sequence including SEQ. ID. NOS. 2-8, described herein. The present disclosure also includes antibodies capable of binding a polypeptide including a sequence selected from SEQ. ID. NOS. 2-8.

Azetidine-2-Carboxylic Acid Inhibitors

The present disclosure also provides methods for treating a patient/host having exposure to Aze (e.g., by ingestion of products containing Aze). Such methods include, but are not limited to, countering the potential deleterious effects of the Aze by preventing at least some incorporation of Aze into the proteins, tissues, and the like. of a patient/host. Such methods include administering to a patient/host in need thereof (e.g., one who has recently ingested Aze-containing materials), in particular a pregnant patient/host, an effective amount of a composition including the amino-acid proline.

The effects of exposure to azetidine-2-carboxylic acid, as occur after ingestion of a food containing the nonprotein amino acid, can be ameliorated by a "washout procedure" in which large amounts of the amino acid proline are ingested or otherwise administered. In a preferred embodiment, The proline reagent is highly purified and substantially free of azetidine-2-carboxylic acid.

For instance, a woman who believes that she may be in the early stages of pregnancy and has eaten a food product that may contain azetidine-2-carboxylic acid would promptly take large amounts of proline to diminish the effects of azetidine-2-carboxylic acid.

Embodiments of the present disclosure include methods of reducing the amount of Aze incorporated into host proteins after consumption by a host of materials including Aze (such as garden beets or milk produced from cattle fed sugar beet byproducts). Such methods include administering to a host who has recently consumed material containing Aze a therapeutically effective amount of a composition including proline, where the proline is effective to reduce the amount of Aze incorporate into host proteins relative to the amount that would otherwise be incorporated into the host proteins. In particular, it is believed that the administration of proline will reduce the amount of Aze incorporated into host proteins such as, but not limited to, myelin basic protein, collagen, hypoxia-inducible factor, profilins, ion channel proteins, vesicular glutamate transporters, and hemoglobins. The proline, preferably substantially pure L-proline, may be combined with a pharmaceutically acceptable carrier or other ingredients, as would be known to those of skill in the art.

For example, an embodiment of a method of treating a patient having recently ingested Aze includes administering (e.g., consuming) an effective amount of a composition containing substantially purified proline. In another embodiment, the host is a pregnant female and the proline is effective to reduce or prevent incorporation of Aze into fetal proteins, thereby reducing the risk of birth defects mediated by Aze misincorporation into fetal proteins.

In yet other embodiments, methods of treating disorders associated with Aze are provided. Such methods include administering to a host in need of treatment for a disorder associated with Aze a therapeutically effective amount of a composition including proline (e.g., substantially pure L-proline), where the proline is effective to reduce the amount of Aze incorporated into host proteins. Exemplary disorders treatable by such methods include, but are not limited to: multiple sclerosis, rheumatoid arthritis, systemic lupus erythematosus, systemic scleroses, mixed connective tissue disorders, and inflammatory myopathies and vasculitides. In particular, disorders treatable with the above methods include auto-immune disorders. Since such disorders may already involve some misincorporation of Aze into host proteins, the methods also include treatment by preventing or reducing additional incorporation of Aze into host proteins, which may aggravate the condition. In embodiments, the host proteins include proteins that play an important role in the above-mentioned disorders such as, but not limited to, myelin basic protein, collagen, hypoxia-inducible factor, profilins, ion channel proteins, vesicular glutamate transporters, and hemoglobins.

In an embodiment, between about 10 to 15 grams of proline is administered (e.g., consumed) by the patient in need thereof. As would be understood by one of skill in the art, the dosage amount will depend on the height, weight, age, health, and condition of the patient. Various dosage forms can be employed including those described below. Dosage forms also may include pharmaceutically acceptable carriers, excipients, diluents, and the like, such as described below.

Compositions including chemical agents that bind strongly to Aze can also be used for treating patients for exposure to Aze, and are included in the present disclosure. Such compounds can be identified by methods known to those of skill in the art. For instance, a library of compounds can be generated and tested for the ability to bind and/or inhibit Aze, such as by assays known to those of skill in the art.

The present disclosure also includes compositions for treating a host having exposure to Aze that include compounds capable of detoxifying (e.g., eliminating, inactivating, and the like) Aze. Such compounds include, but are not limited to compounds capable of inactivating Aze by acetylation, such as Aze acetyltransferases, including, but not limited to, those described above. The present disclosure also includes methods of treating a host/patient having exposure to Aze by administering an effective amount of a pharmaceutical composition including an Aze acetyltransferase.

Pharmaceutical compositions and unit dosage forms typically also include one or more pharmaceutically acceptable excipients or diluents. Advantages provided by such compositions, such as, but not limited to, increased solubility and/or enhanced flow, purity, or stability (e.g., hygroscopicity) characteristics can make them better suited for pharmaceutical formulation and/or administration to patients than those of the prior art.

Pharmaceutical unit dosage forms of the active composition, including proline, are suitable for topical, transdermal, oral, mucosal (e.g., nasal, sublingual, vaginal, buccal, or rectal), or parenteral (e.g., intramuscular, subcutaneous, intravenous, intraarterial, or bolus injection) administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the active composition can vary depending on their use. For example, a dosage form used in the acute treatment of a disease or disorder may contain larger amounts of the active ingredient (e.g., the active composition) than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. (e.g., Remington's Pharmaceutical Sciences, 18th ed., Mack Publishing, Easton, Pa. (1990)).

Typical pharmaceutical compositions and dosage forms can include one or more excipients. Suitable excipients are well known to those skilled in the art of pharmacy or pharmaceutics. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form.

The disclosure further encompasses pharmaceutical compositions and dosage forms that include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of active ingredient (e.g., substantially purified proline) in a dosage form may differ depending on factors such as, but not limited to, the route by which it is to be administered to patients, the condition to be treated, the size of the host, etc. However, typical dosage forms of the compounds of the disclosure include substantially purified proline, a pharmaceutically acceptable salt, or a pharmaceutically acceptable polymorph, solvate, hydrate, dehydrate, co-crystal, anhydrous, or amorphous form thereof, in an amount of from about 5 to 15 grams, preferably from about 10 to 15 grams. The average daily adult intake of proline is believed to be about 5 grams/day. One study of proline administration demonstrated that a 1 mmol proline/kg lean body mass resulted in an approximately 13-fold increase in plasma proline concentration, which would be decreased by half if about 25 g of glucose were also ingested. The study also showed that proline was readily absorbed (Nuttall, F. Q. et al, The metabolic response to ingestion of proline with and without glucose. *Metabolism* 53(2):241-6 (2004), which is hereby incorporated by reference herein). Proline synthesis and degradation is also described in Adams, E. and Frank L. Metabolism of proline and the hydroxyproline. *Ann. Rev. Biochem.* 49:1005-61 (1980).

Due to the increased risk to pregnant hosts of the effects of Aze, the present disclosure also includes pharmaceutical compositions including prenatal formulations (e.g., prenatal vitamins) including proline in an amount from about 5 mg to 15 mg. Such vitamins may be in the dosage forms described above, and may include other common components of prenatal vitamins (e.g., iron, folic acid, calcium, vitamin A, the B vitamins, and the like).

Topical, Transdermal and Mucosal Dosage Forms

Topical dosage forms of the disclosure include, but are not limited to, creams, lotions, ointments, gels, shampoos, sprays, aerosols, solutions, emulsions, and other forms known to one of skill in the art. (e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985)). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. (e.g., Remington's Pharmaceutical Sciences, 18.sup.th Ed., Mack Publishing, Easton, Pa. (1990)).

Transdermal and mucosal dosage forms of the active composition include, but are not limited to, creams, lotions, ointments, gels, solutions, emulsions, suspensions, suppositories, ophthalmic solutions, patches, sprays, aerosols, or other forms known to one of skill in the art. (e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985)). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to, water, phosphate-buffered saline, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of an active composition. For example, penetration enhancers can be used to assist in delivering the active ingredients to or across the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone);

urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of an active composition can be used to further adjust the properties of the resulting composition.

It should be emphasized that the above-described embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure.

EXAMPLES

Now having described the embodiments of the methods, compositions, systems and features of the present disclosure in general, the following examples describe certain embodiments of compositions and methods for detection of Aze in food and embodiments of compositions and methods for Aze containing antigens for use in detection of antibodies to Aze containing proteins and peptides. While such embodiments are described in connection with Examples 1-2 and the corresponding text and figures, there is no intent to limit the embodiments of the present disclosure to these descriptions. On the contrary, the intent is to cover all alternatives, modifications, and equivalents included within the spirit and scope of embodiments of the present disclosure.

Example 1

Azetidine-2-Carboxylic Acid in Milk and in Yeast

As discussed above, Aze is present in table beets and in sugar beets; the latter are the source of about 30% of the world's supply of sucrose. Byproducts of sugar beets leftover from sugar processing are fed to meat and dairy livestock, and in this way their constituents may enter food consumed by humans. The purpose of this example was to determine whether Aze is present in certain foods derived from such livestock and then consumed by humans.

This example presents the results of amino acid analyses of two groups of foods. The first were chosen because they are derived from animals that may have been fed sugar beet byproducts; the second were foods chosen because they have no apparent exposure to sugar beet byproducts.

In addition, two varieties of commercial baker's yeast (*Saccharomyces cerevisiae*) were examined for Aze content. Yeast was included in this study inasmuch as this organism has potential exposure to Aze in sugar beet molasses, which is widely used as a major raw material in yeast production.

Results and Discussion

The analyses were done on food products purchased at random at four different supermarkets located on the San Francisco Peninsula.

Figure 2:
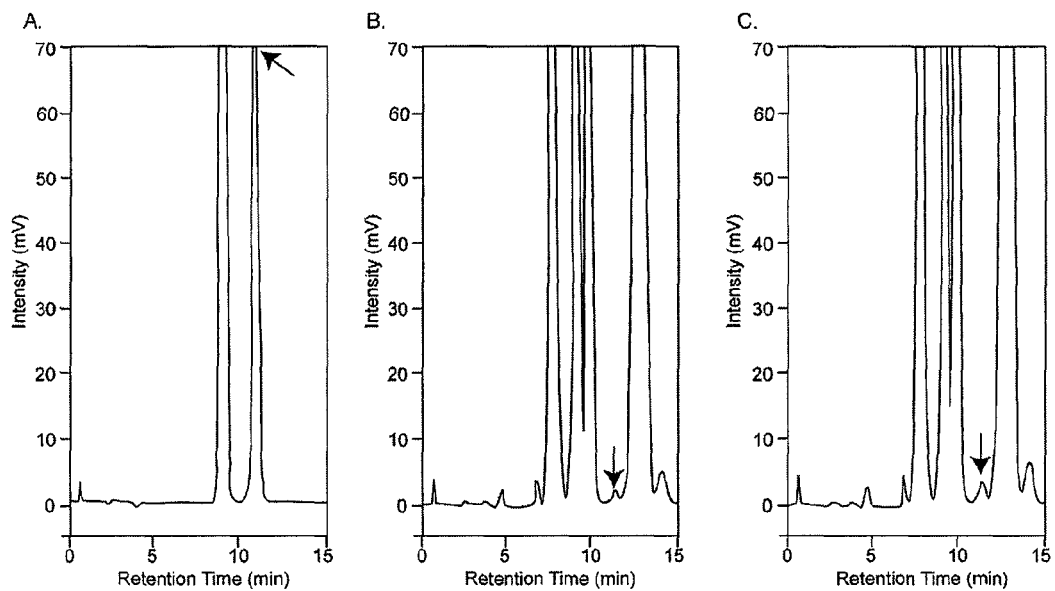
FIG. 2 illustrates chromatographic peaks of (A) pure Aze, (B) liquid milk, and (C) liquid milk spiked with Aze, using a Hitachi L-8800 amino-acid analyzer.

Aze was found to be present in each of two different samples of pooled milk, one a canned fat-free liquid variety, and the other a powdered fat-free dry milk variety, provided by two different suppliers. The findings were confirmed using two different analytic systems, the first a Beckman 6300 amino-acid analyzer, and the second a Hitachi L-8800 amino acid analyzer, as shown in FIG. 2. The concentration of Aze in liquid milk was 0.4 mM.

Figure 3:
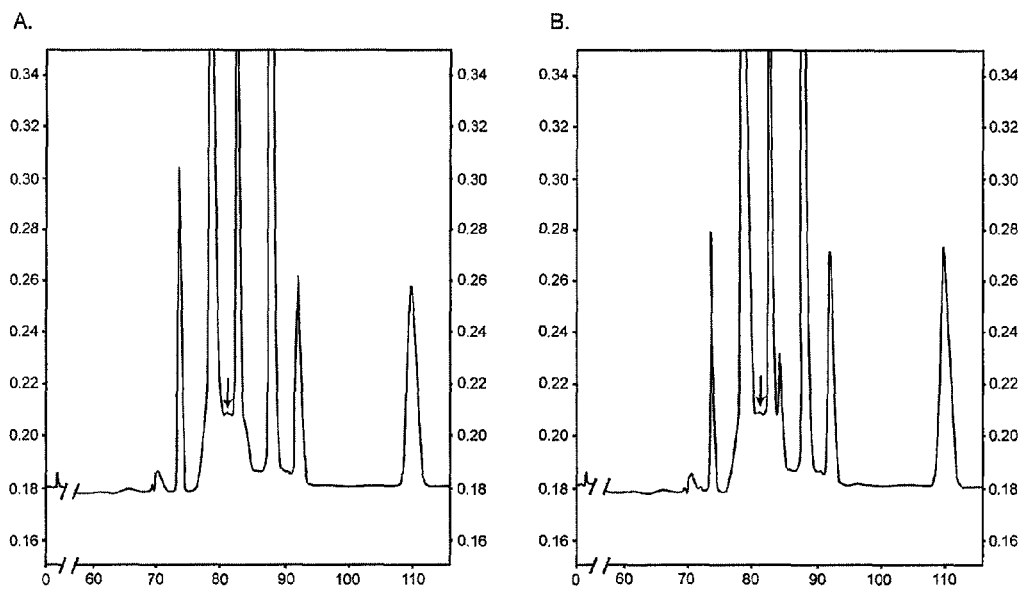
FIG. 3 illustrates chromatographic peaks of two different varieties of yeast (*Saccharomyces cerevisiae*), samples A and B, showing the peaks of Aze in each. The analyses were done using a Beckman (Li) amino-acid analyzer.

This approach was used on two different samples of commercial baker's yeast, one produced in Canada and the other in Mexico. The same two analytic systems were used and in each case Aze was found in *Saccharomyces cerevisiae*, as shown in FIG. 3. The concentration of Aze was 0.08 µM per gram of dry yeast.

The same approach was used for testing potato start, rice flour and tapioca flour. Aze was not found in any of these foods.

These data confirm that Aze is present in bovine dairy products and in commercial yeast. How Aze enters milk is not established. While not wishing to be bound by theory, it is believed that the source may be sugar beet byproducts fed to the livestock. Prospective studies of milk derived from cattle whose diets contain or do not contain sugar beet byproducts can address this issue. Similar studies of yeast can also be performed.

As discussed in detail above, the intrusion of Aze into the food chain has significant implications regarding disease in humans. The misincorporation of Aze in place of proline may be especially pathogenetic when the malformed protein is involved in critical functions such as DNA repair or embryogenesis.

These data indicate that azetidine-2-carboxylic acid is present in dairy products and in yeast. It is believed that entry of this highly toxic and teratogenic nonprotein amino acid into the human food chain relates to the use of sugar beet byproducts as supplemental feed for livestock.

Materials and Methods

The powdered materials (tapioca flour, rice flour, potato starch, nonfat dry milk) and dry samples (e.g., yeasts) were stored at ambient temperature either in the original packages (e.g., dry milk, yeast) or in 15-ml plastic tubes. The canned liquid fat free milk was transferred into two 1.5 ml Eppendorf tubes and stored at −20° C.

All samples were sent for amino acid analysis by 2-day commercial land-based carrier at ambient temperature. All were shipped dry either in their original form or when appropriate after freezing and lyophilization. Tapioca flour, rice flour and potato starch were submitted in their original powder form; liquid milk (100 µl) was frozen and lyophilized; powdered milk (10 mg in 100 µl water) was frozen and lyophilized; both yeast samples were slurried (10 mg in 500 µl water) and sonicated (Branson model 5200 bench-top water bath sonicator) for 1.5 hr with occasional vortexing; then frozen and lyophilized.

The samples were transferred into two 200 µl formic acid transfer glass hydrolysis tubes and then dried. Each sample was them subjected to liquid phase hydrolysis (200 µl, 6 N HCl/0.1% phenol@ 110 C. for 24 hrs), and then dried. Each sample was then dissolved in aminoethyl cysteinyl (AE-Cys) dilution buffer, vortexed, centrifuged, and 50 µl containing 5.0 nmol of the added AE-Cys was loaded in an amount of 50 µl, containing 5.0 nmol of the added AE-Cys.

Each sample was analyzed twice, using two different analytical systems, a Beckman 6300 Li-buffered system and a Hitachi L-8800 (Na-based) machine. A standard injection volume of 50 µl in AE-Cys buffer was used and included norleucine as an internal standard to correct for variations on the operating conditions of the analyzers over time.

Aze remnants were found in the milk and yeast samples using both systems. The same remnants were present in pure Aze samples (Sigma Aldrich catalog # A0760 lot 026K1354; CAS number Aze is 2133-34-8), in Aze-spiked samples, and in milk and yeast samples that were not spiked. The elution times were different for the two analytic systems, 80 minutes for the Beckman system and 11.5 minutes for the Hitachi system. These remnants were not found in any of the other samples. The large difference in elution times indicates the presence of two distinct remnants of Aze in the two analytic systems.

Example 2

Synthesis of Aze-Containing Peptides

In this example a peptide library was prepared, with each peptide nine amino acids in length (to mimic the nonameric antigens that would be presented by a host MHC complex). The following peptides represent derivatives of a nine-amino acid length proline-containing sequence from human myelin basic protein, where one or more of the proline residues has been replaced by Aze. Table 1 below shows the sequence of each peptide. Sequence 1 is amino acids 95 to 103 of wild-type human myelin basic protein, and sequences 2-5 represent derivatives of sequence 1, where one or more of the proline residues have been replaced by Aze.

Peptide Synthesis

Preparation of the above listed peptides (SEQ. ID. NOS: 1-6) was prepared according to established protocol using a Symphony™ peptide synthesizer at the Peptide and Nucleic Acid (PAN) Facility of the Stanford University School of Medicine. The azetidine-2-carboxylic acid used in the synthesis was purchased from ANASPEC, reagent number 20340.

NMR Analysis

Nuclear Magnetic Resonance (NMR) experiments were performed at the Stanford Magnetic Resonance Laboratory (SMRL), a Stanford University School of Medicine research service center. Experiments were performed on a 600 MHz Varian Inova spectrometer equipped with a 5 mm triple resonance H{CN} z-gradient probe and variable temperature control capability, and running VNMR version 6.1C software and the BioPack version 2004-05-13 pulse sequence library.

Peptide samples were synthesized as described above. The peptide sequences provided for NMR analysis are shown in Table 1.

TABLE 1

| SEQ. ID. NO. | Sequence | MW (g/mol) | Mass Provided (mg) |
|---|---|---|---|
| 1 | $NH_2$-T-P-R-T-P-P-P-S-Q-COOH | 980.1 | 1.1 |
| 2 | $NH_2$-T-Az-R-T-P-P-P-S-Q-COOH | 966.0 | 1.0 |
| 3 | $NH_2$-T-P-R-T-Az-Az-Az-S-Q-COOH | 937.79 | 1.0 |

TABLE 1-continued

| SEQ. ID. NO. | Sequence | MW (g/mol) | Mass Provided (mg) |
|---|---|---|---|
| 4 | $NH_2$-T-Az-R-T-Az-P-P-S-Q-COOH | 951.89 | 1.1 |
| 5 | $NH_2$-T-Az-R-T-Az-Az-P-S-Q-COOH | 937.79 | 1.0 |
| 6 | $NH_2$-T-Az-R-T-Az-Az-Az-S-Q-COOH | 923.69 | 1.2 |

Peptide samples were dissolved into 450 µL of aqueous buffer (10 mM sodium phosphate, 100 mM NaCl, pH 6.5) and 50 µL $D_2O$.

Figure 4:
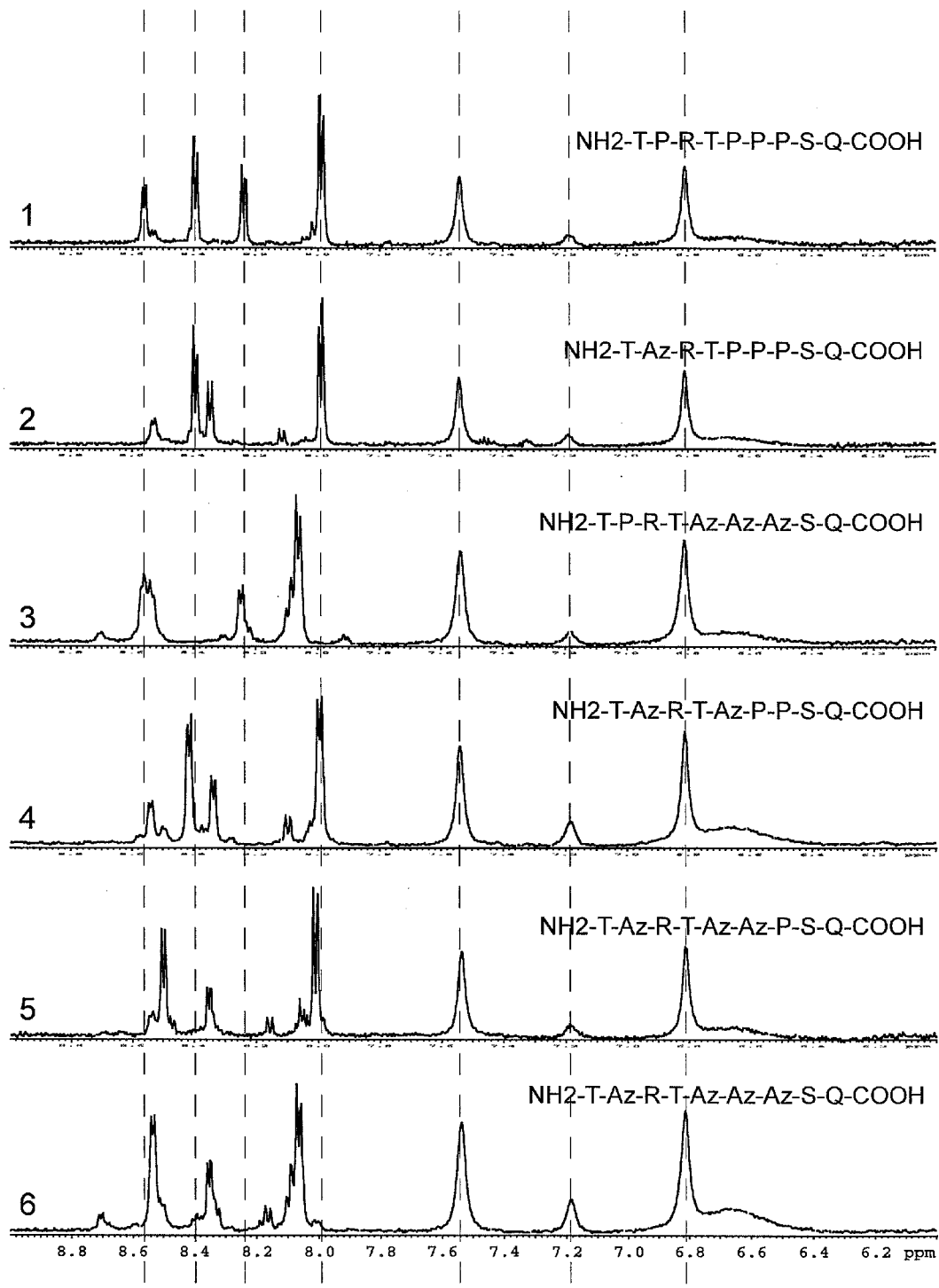
FIG. 4 illustrates NMR spectra of 6 peptide derivatives of myelin basic peptide. Peptide 1 represents amino acids 95 to 103 of a wild-type human myelin basic protein (SEQ. ID. NO. 1). Peptides 2-6 (SEQ. ID. NOS. 2-6) are derivatives of peptide 1 with one or more proline residues replaced with Aze.

One-dimensional proton spectra were collected on each peptide sample at 25° C. using the "water" pulse sequence configured for WET water suppression. Pertinent acquisition parameters utilized were pre-acquisition delay (d1)=1 sec, total data points (np)=8192, number of scans (nt)=16, and spectral width (sw)=8384.86 Hz. Data were processed using 1× zero-filling and an exponential line-broadening (lb) of 1 Hz. The NMR spectra of the six peptides are illustrated in FIG. 4, which is a stacked plot of proton 1-dimensional experiments of the 6 nonameric peptides showing the amide proton region. The vertical dashed lines are aligned with the WT sequence (SEQ. ID. NO. 1) peptide resonances.

Two-dimensional proton spectra were collected on peptide 1 at 25° C. A TOCSY (FIG. 5) was acquired using the "zdipsitocsy" pulse sequence with a mixing time=60 millisec, pre-acquisition delay (d1)=1 sec, direct detected dimension parameters of total data points (np)=8192, number of scans (nt)=16, spectral width (sw)=6000.60 Hz, and indirect detected dimension parameters of number of increments (ni)=256, spectral width (sw1)=6000.60.

A ROESY (FIG. 6) was acquired using the "wroesy" pulse sequence with a mixing time=300 millisec, pre-acquisition delay (d1)=3 sec, direct detected dimension parameters of total data points (np)=8192, number of scans (nt)=16, spectral width (sw)=6000.60 Hz, and indirect detected dimension parameters of number of increments (ni)=256, spectral width (sw1)=6000.60. Data were processed using 1× zero-filling and sine-bell squared apodization functions in both dimensions.

One-dimensional and two-dimensional spectra were also collected on peptide 1 at 15° C. utilizing the same pulse sequences and parameters as at 25° C. except the ROESY pre-acquisition delay was 2 sec, and two additional ROESY experiments (mixings times of 100 and 200 millisec) were acquired. Processing was similar as set forth above. Data is not shown.

Figure 5:
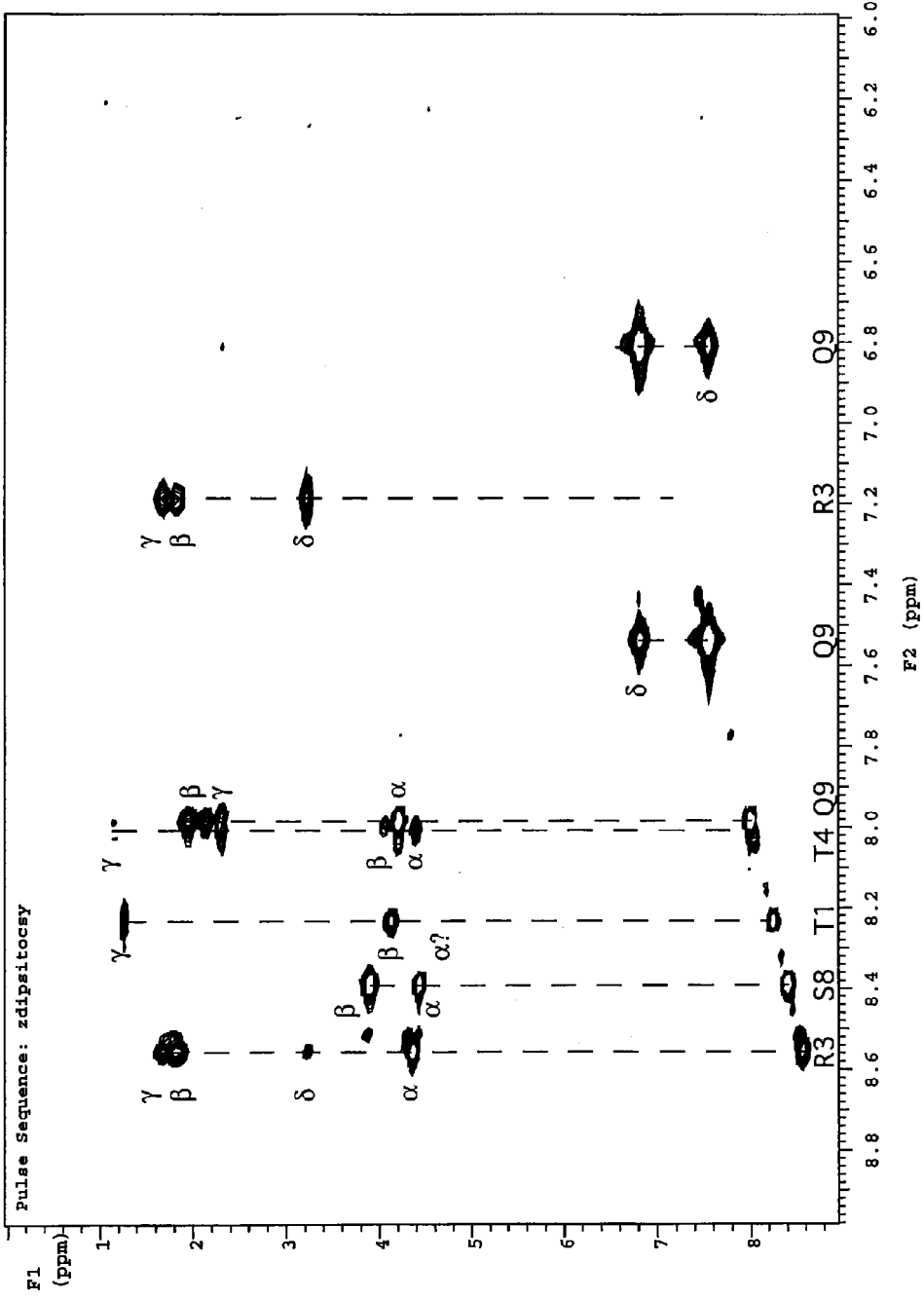
FIG. 5 illustrates a TOCSY two-dimensional proton spectra of peptide 1 (SEQ. ID. NO. 1).
Figure 6:
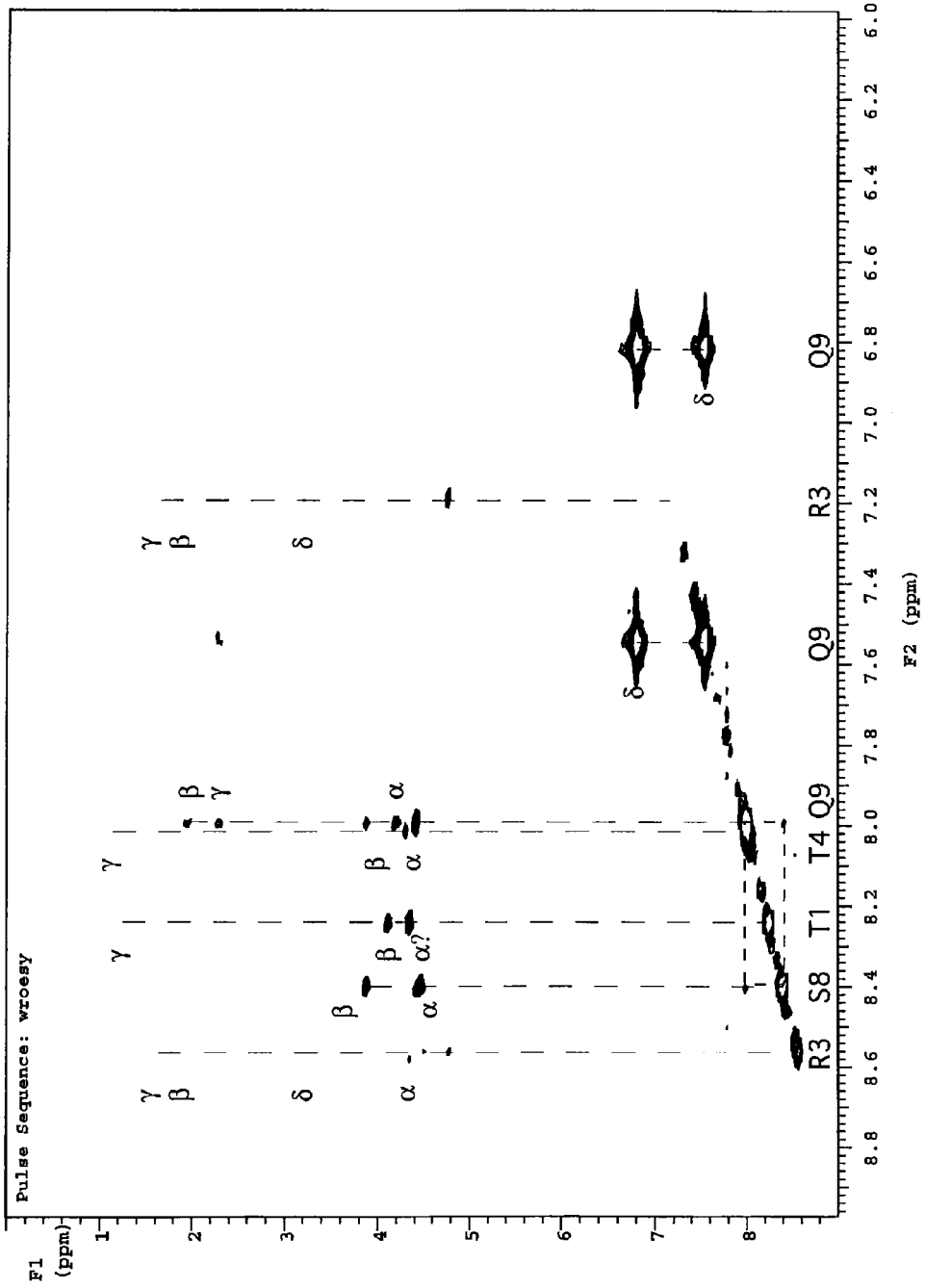
FIG. 6 illustrates a ROESY two-dimensional proton spectra of peptide 1 (SEQ. ID. NO. 1).

FIGS. 5 and 6 illustrate 2-dimensional TOCSY (FIG. 5) and ROESY (FIG. 6) spectra of WT sequence (SEQ. ID. NO. 1) performed at 25° C. Regions shown are the fingerprint regions of the 2-D spectra, consisting of the amide proton region in the F2 (horizontal) dimension and the full spectral range in the F1 (vertical dimension). These spectra were utilized to assign the resonances and are annotated on the figures. Not all side-chain resonances are observed in the ROESY data set likely due to amide proton exchange rates at 25° C., but the resonance assignment labels are carried over from the TOCSY figure.

We claim:

1. A polypeptide consisting of a sequence selected from:
SEQ. ID. NOS. 2-8.

* * * * *

SEQUENCE LISTING

<160> NUMBER OF SEQ ID NOS: 9

<210> SEQ ID NO 1
<211> LENGTH: 9
<212> TYPE: PRT
<213> ORGANISM: Homo sapiens

<400> SEQUENCE: 1

Thr Pro Arg Thr Pro Pro Pro Ser Gln
1               5

<210> SEQ ID NO 2
<211> LENGTH: 9
<212> TYPE: PRT
<213> ORGANISM: artificial sequence
<220> FEATURE:
<223> OTHER INFORMATION: synthetic derivative of amino acids 95 to 103
      of human myelin basic protein
<220> FEATURE:
<221> NAME/KEY: MISC_FEATURE
<222> LOCATION: (2)..(2)
<223> OTHER INFORMATION: Xaa is Azetidine-2-carboxylic acid (AZE)

<400> SEQUENCE: 2

Thr Xaa Arg Thr Pro Pro Pro Ser Gln
1               5

<210> SEQ ID NO 3
<211> LENGTH: 9
<212> TYPE: PRT
<213> ORGANISM: artificial sequence
<220> FEATURE:
<223> OTHER INFORMATION: synthetic derivative of amino acids 95 to 103
      of human myelin basic protein
<220> FEATURE:
<221> NAME/KEY: MISC_FEATURE
<222> LOCATION: (5)..(7)
<223> OTHER INFORMATION: Xaa is Azetidine-2-carboxylic acid (Aze)

<400> SEQUENCE: 3

Thr Pro Arg Thr Xaa Xaa Xaa Ser Gln
1               5

<210> SEQ ID NO 4
<211> LENGTH: 9
<212> TYPE: PRT
<213> ORGANISM: artificial sequence
<220> FEATURE:
<223> OTHER INFORMATION: synthetic derivative of amino acids 95 to 103
      of human myelin basic protein
<220> FEATURE:
<221> NAME/KEY: MISC_FEATURE
<222> LOCATION: (2)..(2)
<223> OTHER INFORMATION: Xaa is Azetidine-2-carboxylic acid (Aze)
<220> FEATURE:
<221> NAME/KEY: MISC_FEATURE
<222> LOCATION: (5)..(5)
<223> OTHER INFORMATION: Xaa is Azetidine-2-carboxylic acid (Aze)

<400> SEQUENCE: 4

Thr Xaa Arg Thr Xaa Pro Pro Ser Gln
1               5

<210> SEQ ID NO 5
<211> LENGTH: 9
<212> TYPE: PRT
<213> ORGANISM: artificial sequence
<220> FEATURE:
<223> OTHER INFORMATION: synthetic derivative of amino acids 95 to 103 of human myelin basic protein
<220> FEATURE:
<221> NAME/KEY: MISC_FEATURE
<222> LOCATION: (2)..(2)
<223> OTHER INFORMATION: Xaa is Azetidine-2-carboxylic acid (Aze)
<220> FEATURE:
<221> NAME/KEY: MISC_FEATURE
<222> LOCATION: (5)..(6)
<223> OTHER INFORMATION: Xaa is Azetidine-2-carboxylic acid (Aze)

<400> SEQUENCE: 5

Thr Xaa Arg Thr Xaa Xaa Pro Ser Gln
1               5

<210> SEQ ID NO 6
<211> LENGTH: 9
<212> TYPE: PRT
<213> ORGANISM: artificial sequence
<220> FEATURE:
<223> OTHER INFORMATION: synthetic derivative of amino acids 95 to 103
      of human myelin basic protein
<220> FEATURE:
<221> NAME/KEY: MISC_FEATURE
<222> LOCATION: (2)..(2)
<223> OTHER INFORMATION: Xaa is Azetidine-2-carboxylic acid (Aze)
<220> FEATURE:
<221> NAME/KEY: MISC_FEATURE
<222> LOCATION: (5)..(7)
<223> OTHER INFORMATION: Xaa is Azetidine-2-carboxylic acid (Aze)

<400> SEQUENCE: 6

Thr Xaa Arg Thr Xaa Xaa Xaa Ser Gln
1               5

<210> SEQ ID NO 7
<211> LENGTH: 9
<212> TYPE: PRT
<213> ORGANISM: artificial sequence
<220> FEATURE:
<223> OTHER INFORMATION: synthetic derivative of amino acids 95 to 103
      of human myelin basic protein
<220> FEATURE:
<221> NAME/KEY: MISC_FEATURE
<222> LOCATION: (5)..(6)
<223> OTHER INFORMATION: Xaa is Azetidine-2-carboxylic acid (Aze)

<400> SEQUENCE: 7

Thr Pro Arg Thr Xaa Xaa Pro Ser Gln
1               5

<210> SEQ ID NO 8
<211> LENGTH: 9
<212> TYPE: PRT
<213> ORGANISM: artificial sequence
<220> FEATURE:
<223> OTHER INFORMATION: synthetic derivative of amino acids 95 to 103
      of human myelin basic protein
<220> FEATURE:
<221> NAME/KEY: MISC_FEATURE
<222> LOCATION: (5)..(5)
<223> OTHER INFORMATION: Xaa is Azetidine-2-carboxylic acid (Aze)

<400> SEQUENCE: 8

Thr Pro Arg Thr Xaa Pro Pro Ser Gln
1               5

<210> SEQ ID NO 9
<211> LENGTH: 6
<212> TYPE: PRT
<213> ORGANISM: Homo sapiens
<220> FEATURE:
<221> NAME/KEY: MISC_FEATURE

```
<222> LOCATION: (2)..(3)
<223> OTHER INFORMATION: Xaa can be any amino acid

<400> SEQUENCE: 9

Leu Xaa Xaa Leu Ala Pro
1               5
```